US006752794B2

(12) United States Patent
Lockwood et al.

(10) Patent No.: US 6,752,794 B2
(45) Date of Patent: *Jun. 22, 2004

(54) VACUUM THERAPY AND CLEANSING DRESSING FOR WOUNDS

(75) Inventors: Jeffrey S. Lockwood, Batesville, IN (US); Robert Petrosenko, Batesville, IN (US); James R. Risk, Jr., Fountaintown, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/994,537

(22) Filed: Nov. 27, 2001

(65) Prior Publication Data

US 2002/0082567 A1 Jun. 27, 2002

Related U.S. Application Data

(63) Continuation-in-part of application No. 09/725,352, filed on Nov. 29, 2000.

(51) Int. Cl.⁷ .................................................. A61M 1/00
(52) U.S. Cl. ....................................................... 604/313
(58) Field of Search ................................ 604/289, 304, 604/305, 307, 308, 313, 315–318, 327, 543; 602/43, 59

(56) References Cited

U.S. PATENT DOCUMENTS

| 774,529 A | 11/1904 | Nieschang |
| 1,000,001 A | 8/1911 | Holz |
| 1,355,846 A | 10/1920 | Rannells |
| 1,385,346 A | 7/1921 | Taylor |

(List continued on next page.)

FOREIGN PATENT DOCUMENTS

| CA | 2303085 | 9/1997 |
| DE | 0372727 | 3/1923 |
| DE | 28 09 828 | 9/1978 |
| DE | 3102674 A1 | 9/1982 |

(List continued on next page.)

OTHER PUBLICATIONS

Morykwas, et al., Extracellular Matric and Healing 1993, pp. 800—"Use of Negative Pressure to Increase the Rate of Granulation Tissue Formation in Chronic Open Wounds".
Medical Industry Week—article "KCI Offers New Treatment for Non–Healing Wounds".
Brochure—Hiblow Air Pump.
Brochure—Wells Johnson Company—Point 5 Aspirator.
Brochure—Microtek Heritage, Inc.—The Wound Evac ET, Closed Wound Suction System.
Brochure—KCI—The V.A.C. (Vacuum Assisted Closure).
Brochure—Augustine Medical, Warm–Up Active Wound Therapy Wound Covers, 1999.
Brochure—Series 55—Emerson Post–Operative Suction Pumps.

(List continued on next page.)

Primary Examiner—Weilun Lo
Assistant Examiner—Michael G Bogart
(74) Attorney, Agent, or Firm—Barnes & Thornburg

(57) ABSTRACT

A thin, flexible member is provided for use in a vacuum bandage connected to a vacuum source. The member is provided for use with a wound having a wound surface. The member includes a wound contacting surface adapted to be in contact with and generally conform to the wound surface. The member further includes a plurality of discrete holes formed in the wound contacting surface, a port configured to communicate with the vacuum source, and communicating means from the holes to the port. The member is formed from a generally non-porous material.

37 Claims, 17 Drawing Sheets

U.S. PATENT DOCUMENTS

| | | |
|---|---|---|
| 1,936,129 A | 11/1933 | Fisk |
| 2,195,771 A | 4/1940 | Estler |
| 2,221,758 A | 11/1940 | Eimquist |
| 2,338,339 A | 1/1944 | LaMere et al. |
| 2,443,481 A | 6/1948 | Sene |
| 2,573,791 A | 11/1951 | Howells |
| 2,577,945 A | 12/1951 | Atherton |
| 2,632,443 A | 3/1953 | Lesher |
| 2,682,873 A | 7/1954 | Evans et al. |
| 3,026,874 A | 3/1962 | Stevens |
| 3,315,665 A | 4/1967 | MacLeod |
| 3,367,332 A | 2/1968 | Groves |
| 3,382,867 A | 5/1968 | Reaves |
| 3,520,300 A | 7/1970 | Flower, Jr. |
| 3,528,416 A | 9/1970 | Chamberlain |
| 3,610,238 A | 10/1971 | Rich, Jr. |
| 3,648,692 A | 3/1972 | Wheeler |
| 3,782,377 A | 1/1974 | Rychlik |
| 3,812,972 A | 5/1974 | Rosenblum |
| 3,814,095 A | 6/1974 | Lubens |
| 3,874,387 A | 4/1975 | Barbieri |
| 3,903,882 A | 9/1975 | Augurt |
| 3,935,863 A | 2/1976 | Kliger |
| 3,954,105 A | 5/1976 | Nordby et al. |
| 4,080,970 A | 3/1978 | Miller |
| 4,112,947 A | 9/1978 | Nehring |
| 4,139,004 A | 2/1979 | Gonzalez, Jr. |
| 4,149,541 A | 4/1979 | Gammons et al. |
| 4,224,941 A | 9/1980 | Stivala |
| 4,250,882 A | 2/1981 | Adair |
| 4,275,721 A | 6/1981 | Olson |
| 4,297,995 A | 11/1981 | Golub |
| 4,341,209 A | 7/1982 | Schaar |
| 4,373,519 A | 2/1983 | Errede et al. |
| 4,382,441 A | 5/1983 | Svedman |
| 4,399,816 A | 8/1983 | Spangler |
| 4,457,755 A | 7/1984 | Wilson |
| 4,460,370 A | 7/1984 | Allison et al. |
| 4,465,062 A | 8/1984 | Versaggi et al. |
| 4,469,092 A | 9/1984 | Marshall et al. |
| 4,525,166 A | 6/1985 | Leclerc |
| 4,533,352 A | 8/1985 | Van Beek et al. |
| 4,540,412 A | 9/1985 | Van Overloop |
| 4,553,967 A | 11/1985 | Ferguson et al. |
| 4,569,674 A | 2/1986 | Phillips et al. |
| 4,573,965 A | 3/1986 | Russo |
| 4,579,555 A | 4/1986 | Russo |
| 4,605,399 A | 8/1986 | Weston et al. |
| 4,608,041 A | 8/1986 | Nielsen |
| 4,624,656 A | 11/1986 | Clark et al. |
| 4,633,863 A | 1/1987 | Filips et al. |
| 4,637,819 A | 1/1987 | Ouellette et al. |
| 4,641,643 A | 2/1987 | Greer |
| 4,655,754 A | 4/1987 | Richmond et al. |
| 4,661,093 A | 4/1987 | Beck et al. |
| 4,664,652 A | 5/1987 | Weilbacher |
| 4,667,666 A | 5/1987 | Fryslie |
| 4,679,590 A | 7/1987 | Hergenroeder |
| 4,717,332 A | 1/1988 | Edens |
| 4,733,659 A | 3/1988 | Edenbaum et al. |
| 4,743,232 A | 5/1988 | Kruger |
| 4,747,166 A | 5/1988 | Kuntz |
| 4,759,354 A | 7/1988 | Quarfoot |
| 4,765,316 A | 8/1988 | Marshall |
| 4,778,446 A | 10/1988 | Jensen |
| 4,778,456 A | 10/1988 | Lokken |
| 4,820,265 A | 4/1989 | DeSatnick et al. |
| 4,820,284 A | 4/1989 | Hauri |
| 4,834,110 A | 5/1989 | Richard |
| 4,872,450 A | 10/1989 | Austad |
| 4,890,608 A | 1/1990 | Steer |
| 4,897,081 A | 1/1990 | Poirier et al. |
| 4,906,240 A | 3/1990 | Reed et al. |
| 4,917,112 A | 4/1990 | Kalt |
| 4,921,492 A | 5/1990 | Schultz et al. |
| 4,941,882 A | 7/1990 | Ward et al. |
| 4,953,565 A | 9/1990 | Tachibana et al. |
| 4,962,761 A | 10/1990 | Golden |
| 4,969,880 A | 11/1990 | Zamierowski |
| 4,969,881 A | 11/1990 | Viesturs |
| 4,988,336 A | 1/1991 | Kohn |
| 4,990,144 A | 2/1991 | Blott |
| 4,991,574 A | 2/1991 | Pocknell |
| 4,997,425 A | 3/1991 | Shioya et al. |
| 5,002,528 A | 3/1991 | Palestrant |
| 5,002,529 A | 3/1991 | Cunningham |
| 5,003,971 A | 4/1991 | Buckley |
| 5,014,389 A | 5/1991 | Ogilvie et al. |
| 5,034,003 A | 7/1991 | Denance |
| 5,034,006 A | 7/1991 | Hosoda et al. |
| 5,042,978 A | 8/1991 | Quenin et al. |
| 5,060,662 A | 10/1991 | Farnswoth, III |
| 5,073,172 A | 12/1991 | Fell |
| 5,086,763 A | 2/1992 | Hathman |
| 5,086,764 A | 2/1992 | Gilman |
| 5,100,396 A | 3/1992 | Zamierowski |
| 5,106,362 A | 4/1992 | Gilman |
| 5,106,629 A | 4/1992 | Cartmell et al. |
| 5,135,518 A | 8/1992 | Vera |
| 5,147,338 A | 9/1992 | Lang et al. |
| 5,149,331 A | 9/1992 | Ferdman et al. |
| 5,152,757 A | 10/1992 | Eriksson |
| 5,160,322 A | 11/1992 | Scheremet et al. |
| 5,167,613 A | 12/1992 | Karami et al. |
| 5,170,781 A | 12/1992 | Loomis |
| 5,176,663 A | 1/1993 | Svedman et al. |
| 5,176,667 A | 1/1993 | DeBring |
| 5,215,539 A | 6/1993 | Schoolman |
| 5,228,431 A | 7/1993 | Giarretto |
| 5,230,350 A | 7/1993 | Fentress |
| 5,261,893 A | 11/1993 | Zamierowski |
| 5,263,922 A | 11/1993 | Sova et al. |
| 5,298,015 A | 3/1994 | Komatsuzaki et al. |
| 5,330,452 A | 7/1994 | Zook |
| 5,344,415 A | 9/1994 | DeBusk et al. |
| 5,349,965 A | 9/1994 | McCarver |
| 5,358,494 A | 10/1994 | Svedman |
| 5,376,252 A | 12/1994 | Ekstrom et al. |
| 5,395,315 A | 3/1995 | Griep |
| 5,431,622 A | 7/1995 | Pyrozyk et al. |
| 5,437,651 A | 8/1995 | Todd et al. |
| 5,445,604 A | 8/1995 | Lang |
| 5,451,215 A | 9/1995 | Wolter |
| 5,478,333 A | 12/1995 | Asherman, Jr. |
| 5,484,427 A | 1/1996 | Gibbons |
| 5,487,889 A | 1/1996 | Eckert et al. |
| 5,527,293 A | 6/1996 | Zamierowski |
| 5,531,670 A | 7/1996 | Westby et al. |
| 5,542,918 A | 8/1996 | Atkinson |
| 5,549,584 A | 8/1996 | Gross |
| 5,556,375 A | 9/1996 | Ewall |
| 5,578,022 A | 11/1996 | Scherson et al. |
| 5,607,388 A | 3/1997 | Ewall |
| 5,628,735 A | 5/1997 | Skow |
| 5,636,643 A | 6/1997 | Argenta et al. |
| 5,645,081 A | 7/1997 | Argenta et al. |
| 5,655,258 A | 8/1997 | Heintz |
| 5,656,027 A | 8/1997 | Ellingboe |
| 5,662,598 A | 9/1997 | Tobin |
| 5,662,624 A | 9/1997 | Sundstrom et al. |
| 5,662,625 A | 9/1997 | Westwood |

| | | |
|---|---|---|
| 5,678,564 A | 10/1997 | Lawrence et al. |
| 5,697,920 A | 12/1997 | Gibbons |
| 5,735,833 A | 4/1998 | Olson |
| 5,762,640 A | 6/1998 | Kajiwara et al. |
| 5,782,871 A | 7/1998 | Fujiwara et al. |
| 5,817,145 A | 10/1998 | Augustine et al. |
| 5,827,246 A | 10/1998 | Bowen |
| 5,911,222 A | 6/1999 | Lawrence et al. |
| 5,919,476 A | 7/1999 | Fischer et al. |
| 5,921,972 A | 7/1999 | Skow |
| 5,928,174 A | 7/1999 | Gibbins |
| 5,941,859 A | 8/1999 | Lerman |
| 5,947,914 A | 9/1999 | Augustine |
| 5,954,680 A | 9/1999 | Augustine |
| 5,961,480 A | 10/1999 | Augustine |
| 5,964,721 A | 10/1999 | Augustine |
| 5,964,723 A | 10/1999 | Augustine |
| 5,986,163 A | 11/1999 | Augustine |
| 6,010,527 A | 1/2000 | Augustine et al. |
| 6,045,518 A | 4/2000 | Augustine |
| 6,045,541 A | 4/2000 | Matsumoto et al. |
| 6,071,254 A | 6/2000 | Augustine |
| 6,071,267 A | 6/2000 | Zamierowski |
| 6,071,304 A | 6/2000 | Augustine et al. |
| 6,080,189 A | 6/2000 | Augustine et al. |
| 6,080,243 A | 6/2000 | Insley et al. |
| 6,093,160 A | 7/2000 | Augustine et al. |
| 6,095,992 A | 8/2000 | Augustine |
| 6,110,197 A | 8/2000 | Augustine et al. |
| 6,113,561 A | 9/2000 | Augustine |
| 6,117,111 A | 9/2000 | Fleischmann |
| 6,135,116 A | 10/2000 | Vogel et al. |
| 6,142,982 A | 11/2000 | Hunt et al. |
| 6,143,945 A | 11/2000 | Augustine et al. |
| 6,174,306 B1 | 1/2001 | Fleischmann |
| 6,203,563 B1 | 3/2001 | Fernandez |
| 6,207,875 B1 | 3/2001 | Lindqvist et al. |
| 6,213,965 B1 | 4/2001 | Augustine et al. |
| 6,213,966 B1 | 4/2001 | Augustine |
| 6,217,535 B1 | 4/2001 | Augustine |
| 6,235,009 B1 | 5/2001 | Skow |
| 6,235,047 B1 | 5/2001 | Augustine et al. |
| 6,293,917 B1 | 5/2001 | Skow |
| 6,241,697 B1 | 6/2001 | Augustine |
| 6,241,698 B1 | 6/2001 | Augustine |
| 6,248,084 B1 | 6/2001 | Augustine et al. |
| 6,254,557 B1 | 7/2001 | Augustine et al. |
| 6,254,580 B1 | 7/2001 | Svedman |
| 6,264,622 B1 | 7/2001 | Augustine |
| 6,264,979 B1 | 7/2001 | Svedman |
| 6,267,740 B1 | 7/2001 | Augustine et al. |
| 6,283,931 B1 | 9/2001 | Augustine |
| 6,284,941 B1 | 9/2001 | Cox et al. |
| 6,290,685 B1 | 9/2001 | Insley et al. |
| 6,345,623 B1 | 2/2002 | Heaton et al. |
| 2001/0029956 A1 | 10/2001 | Argenta et al. |

FOREIGN PATENT DOCUMENTS

| | | |
|---|---|---|
| DE | 3539533 A1 | 5/1987 |
| DE | 4111122 A1 | 4/1993 |
| DE | 0 880 953 A2 | 2/1998 |
| DE | 19722075 C1 | 10/1998 |
| DK | 0064055 | 10/1945 |
| EP | 0 117 632 A2 | 9/1984 |
| EP | 0 424 165 A1 | 4/1991 |
| EP | 0 485 657 A1 | 5/1992 |
| EP | 0 547 496 A1 | 6/1993 |
| EP | 0880953 A2 | 2/1998 |
| EP | 0 853 950 A1 | 7/1998 |
| EP | 0 777 504 B1 | 10/1998 |
| EP | 0 880 953 A2 | 12/1998 |
| EP | 1 088 569 A2 | 4/2001 |
| FR | 500253 | 3/1920 |
| FR | 1303238 | 7/1962 |
| GB | 641061 | 8/1950 |
| GB | 1 549 756 | 8/1979 |
| GB | 2 329 127 A | 3/1999 |
| GB | 2 333 965 A | 8/1999 |
| GB | 2 336 546 A | 10/1999 |
| GB | 2 342 584 A | 4/2000 |
| GB | 2 344 531 A | 6/2000 |
| GB | 2 351 025 A | 12/2000 |
| GB | 3090 | 6/2002 |
| SE | 0084485 | 10/1935 |
| SU | 587941 | 1/1978 |
| SU | 1268175 A1 | 11/1986 |
| WO | WO 89/04158 | 5/1989 |
| WO | WO 90/11795 | 10/1990 |
| WO | WO 91/00718 | 1/1991 |
| WO | WO 91/16030 | 10/1991 |
| WO | WO 92/19313 | 11/1992 |
| WO | WO 92/20299 | 11/1992 |
| WO | WO 93/09727 | 5/1993 |
| WO | WO 94/00090 | 1/1994 |
| WO | WO 94/20041 | 9/1994 |
| WO | WO 96/05873 | 2/1996 |
| WO | WO 96/15745 | 5/1996 |
| WO | WO 99/13793 | 3/1999 |
| WO | WO 00/07653 | 2/2000 |
| WO | WO 00/15277 | 3/2000 |
| WO | WO 00/21586 | 4/2000 |
| WO | WO 00/26100 | 5/2000 |
| WO | WO 00/30567 | 6/2000 |
| WO | WO 00/32247 | 6/2000 |
| WO | WO 00/38552 | 7/2000 |
| WO | WO 00/38755 | 7/2000 |
| WO | WO 00/42958 | 7/2000 |
| WO | WO 00/59418 | 10/2000 |
| WO | WO 00/59424 | 10/2000 |
| WO | WO 00/61206 | 10/2000 |
| WO | WO 00/64394 | 11/2000 |
| WO | WO 01/34223 A1 | 5/2001 |
| WO | WO 01/37922 A2 | 5/2001 |
| WO | WO 01/49233 A1 | 7/2001 |
| WO | WO 01/85248 A1 | 11/2001 |

OTHER PUBLICATIONS

Brochure—Emerson Transport Suction Unit.

Davydov, et al., Vestn. Khir., Sep. 1988—"Vacuum Therapy in the Treatment of Acute Suppurative Diseases of Soft Tissues and Suppurative Wounds"—(English translation by R. McElroy Translation Co., Austin, Texas).

Davydov, et al., Khirurgiia, Jun. 1990—"Pathogenic Mechanism of the Effect of Vacuum Therapy on the Course of the Wound Process" (English translation by R. McElroy Translation Co., Austin, Texas).

Davydov, et al., Vestn. Khir., Nov. 1986—"Vacuum Therapy in the Treatment of Suppurative Lactation Mastitis" (English translation by R. McElroy Translation Co., Austin, Texas).

Davydov, et al., Vestn. Khir., Oct. 1988—"Bacteriological and Cytological Evaluation of the Vacuum Therapy of Suppurative Wounds" (English translation by R. McElroy Translation Co., Austin Texas).

Davydov, et al., Vestn. Khir., Mar. 1990—"Basis of the Use of Forced Early Secondary Suture in the Treatment of Suppurative Wounds" (English translation by R. McElroy Translation Co., Austin Texas).

Mirazimov, et al., Ortop Travmatol Protez., Oct. 1966—"Free Skin Graft of the Foot with Preparation of the Wound Surface by Vacuum Treatment" (English translation by R. McElroy Translation Co., Austin, Texas).

Borzov, et al., Vestn. Dermatol. Venerol, Aug. 1965—"Vacuum Therapy of Some Skin Diseases" (English translation by R. McElroy Translation Co., Austin, Texas).

Jeter, et al., Chronic Wound Care; 27: pp. 240–246—"Managing Draining Wounds and Fistulae: New and Established Methods".

Mulder, et al., Wound Healing Publications 1991—"Clinicians' Pocket Guide to Chronic Wound Repair".

Valenta, AIN Apr. 1994; pp. 44–45—"Using the Vacuum Dressing Alternative for Difficult Wounds".

Wolthuis, et al., Physiological Reviews Jul. 1974; vol. 54, No. 3, pp. 566–595—"Physiological Effects of Locally Applied Reduced Pressure in Man".

Fleischmann—WundForum Spezial IHA 1994; pp. 54–55—"Vacuum Sealing for Treatment of Problematical Wounds" (English translation provided).

Bucalo, et al., Wound Repair and Regeneration; Jul.–Sep. 1993; pp. 181–186—"Inhibition of Cell Proliferation by Chronic Wound Fluid".

Olenius, et al., Plastic and Reconstructive Surgery Feb. 19931; pp. 213–215—"Mitotic Activity in Expanded Human Skin".

Viljanto, et al., Br. J. Surg. 1976; vol. 63: pp. 427–430—"Local Hyperalimentation of Open Wounds".

Dunlop, et al., Fr. J. Surg. May 1990; vol. 77: pp. 562–563—"Vacuum Drainage of Groin Wounds after Vascular Surgery: A Controlled Trial".

Comment–Dunlop et al., Apr. 1991, pp. 505–506 on "Vacuum Drainage of Groin Wounds after Vascular Surgery".

Landis, et al., Alternate Suction and Pressure, pp. 925–961—"The Effects of Alternate Suction and Pressure on Blood Flow to the Lower Extremities".

Svedman, et al., Annals of Plastic Surgery Aug. 1986; vol. 17, No. 2: pp. 125–133—"A Dressing System Providing Fluid Supply and Suction Drainage Used for Continuous or Intermittent Irrigation".

Schneider, et al., Plastic and Reconstructive Surgery Sep. 1998, pp. 1195–1198—"A New and Reliable Method of Securing Skin Grafts to the Difficult Recipient Bed".

Morykwas, et al., www.sma.org/soa/jsoawt97—"Nonsurgical Modalities to Enhance Healing and Care of Soft Tissue Wounds".

Chariker, et al., Contemporary Surgery Jun. 1989; vol. 34: pp. 59–63—"Effective Management of Incisional and Cutaneous Fistulae with Closed Suction Wound Drainage".

Tittel, Eingag und Annahme des Manuskripts, Jan. 7, 1987, pp. 104–107—"New Standards in Postoperative Wound Drainage".

Genecov, et al., Annals of Plastic Surgery Mar. 1998, vol. 40, No. 3: pp. 219–225—"A Controlled Sub–atmospheric Pressure Dressing Increases the Rate of Skin Graft Donor Site Reepithelialization".

Morykwas, et al., Annals of Plastic Surgery Jun. 1997; vol. 38, No. 6—"Vacuum–Assisted Closure: A New Method for Wound Control and Treatment: Animal Studies and Basic Foundation".

Argenta, et al., Annals of Plastic Surgery Jun. 1997; vol. 38, No. 6—"Vacuum–Assisted Closure: A New Method for Wound Control and Treatment: Clinical Experience".

Patent Application and Drawings—"Method of Treating Tissue Damage and Apparatus for Same" consisting of 28 pages.

Patent Application and Drawings—"The Enhancement of Wound Healing and Flap Survival by a New Negative Pressure Device", Argenta et al., consisting of 30 pages.

Nakayama, et al., Ann Plast Surg. May 1991; vol. 26, No. 5: pp. 499–502—"A New Dressing of Wound Healing and Flap Survival by a New Negative Pressure Device".

Nakayama, et al., Plast. Reconstr. Surg. Dec. 1990; vol. 86 No. 6 pp. 1216–1219—"A New Method for the Dressing of Free Skin Grafts".

Sames, Br. Med. J. Nov. 5, 1977; vol. 2, No. 6096: 1123—"Sealing of Wounds with Vacuum Drainage".

Fleishmann, et al., Unfallchirurg, 1993; 96:488–492—"Vacuum Sealing for Treatment of Soft Tissue Injury in Open Fractures" (English translation of the Summary provided).

Teder, et al., J. of Invest. Surg. 1990; vol. 3: pp. 399–407—"Continuous Wound Irrigation in the Pig".

Wood, et al., Br. J. of Surg. 1977; vol. 64: pp. 554–557—"Foam Elastomer Dressing in the Management of Open Granulating Wounds: Experience with 250 Patients".

Neumann, et al., J. of Biomed. Materials Research 1981; vol. 15: pp. 9–18—"Gelatin–Based Sprayable Foam as a Skin Susbstitute".

Kostluchenok et al., Vestn. Khir. Sep. 1986—"Vacuum Treatment in the Surgical Treatment of Suppurative Wounds" (English translation by R. McElroy Translation Co., Austin, Texas).

Lundvall, et al., Acta. Physiol. Scand. 1989; vol. 136: pp. 403–409—"Transmission of Externally Applied Negative Pressure to the Underlying Tissue. A Study on the Upper Arm of Man".

Brochure—Aeros—Instavac Aspirator.

Brochure—Pluer-Evac Adult-Pediatric—Non-Metered Disposable "3–Bottle" Unit, A–4000.

Brochure—Aeros—Care-E-Vac.

Brochure—Aeros—MoblvacII.

Bochure/Instruction Manual—Creative Medical Laboratories, Inc., —TUGS (Transportable Universal Gradient Suction) System.

Brochure—Microtek Heritage, Inc.13 The Wound Evac ET, Closed Wound Suction System.

Brochure—Augustine Medical, Warm–Up Active Wound Therapy Wound Covers, 1999.

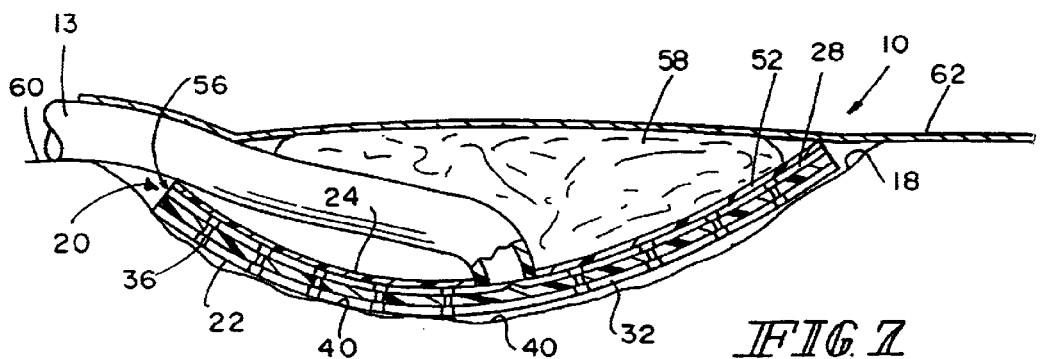
FIG. 7
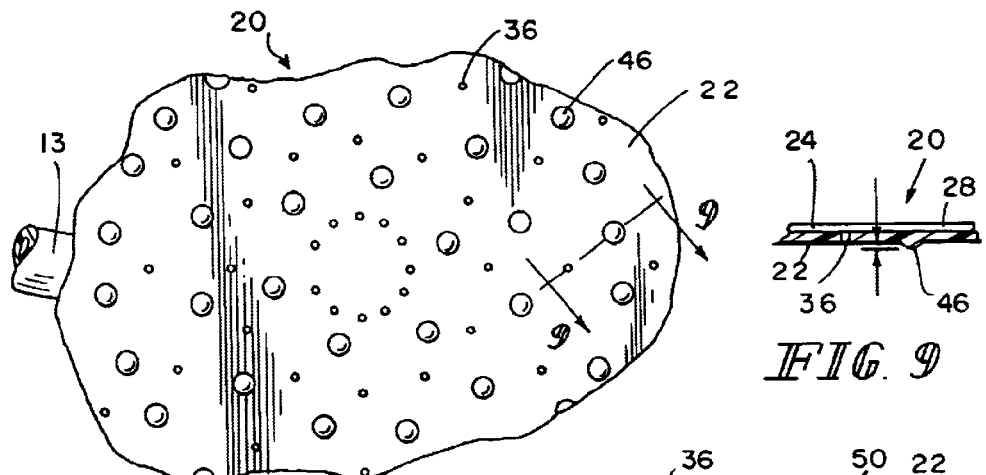
FIG. 8
FIG. 9
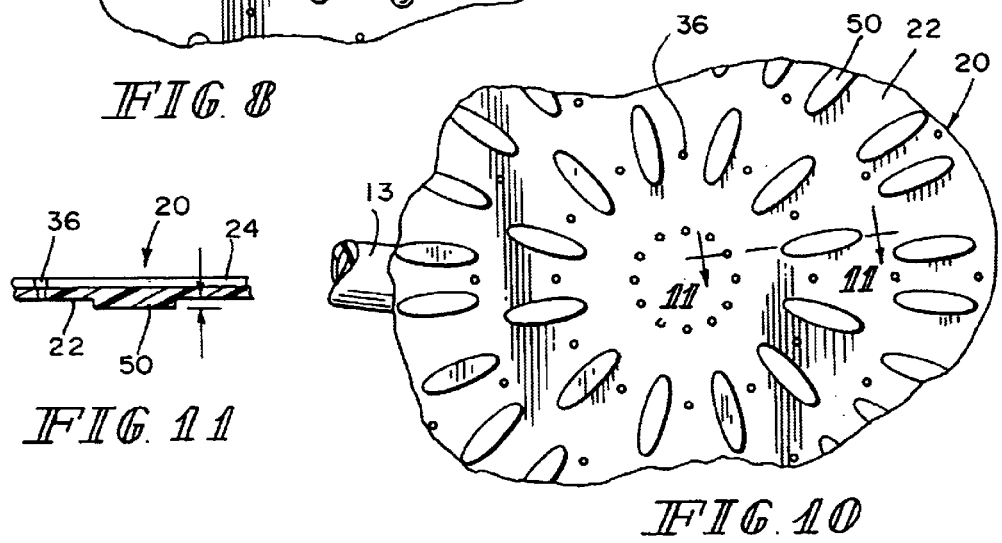
FIG. 11
FIG. 10

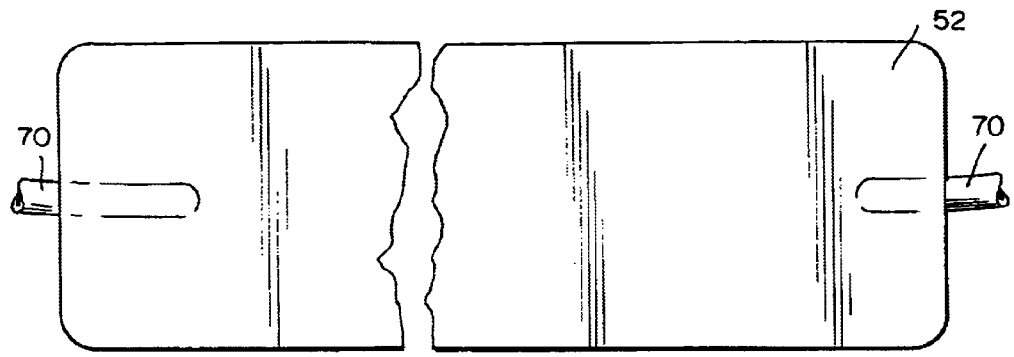
FIG. 12
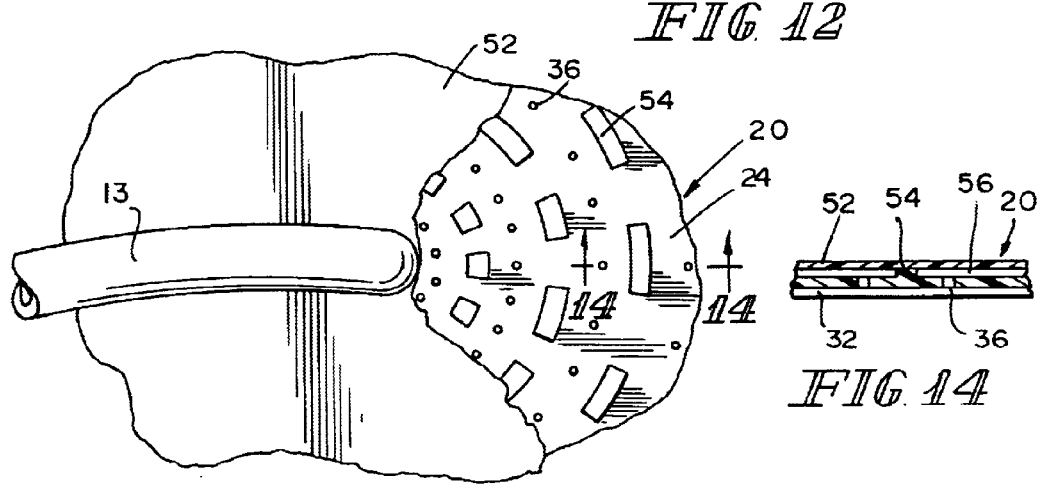
FIG. 13
FIG. 14
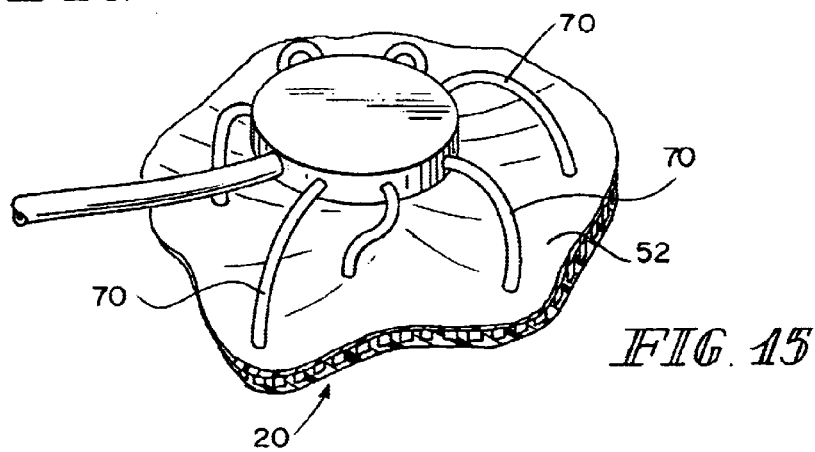
FIG. 15

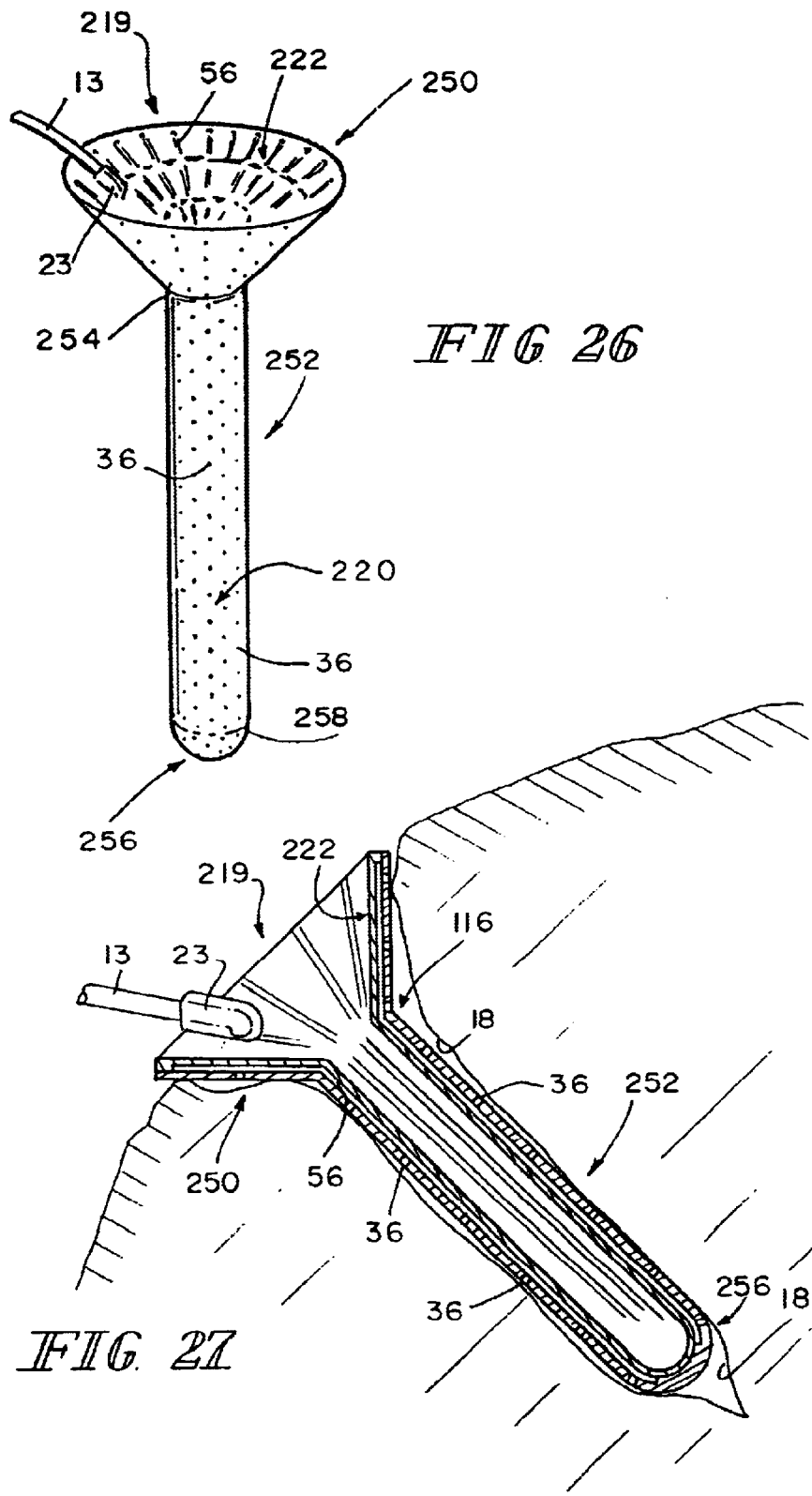

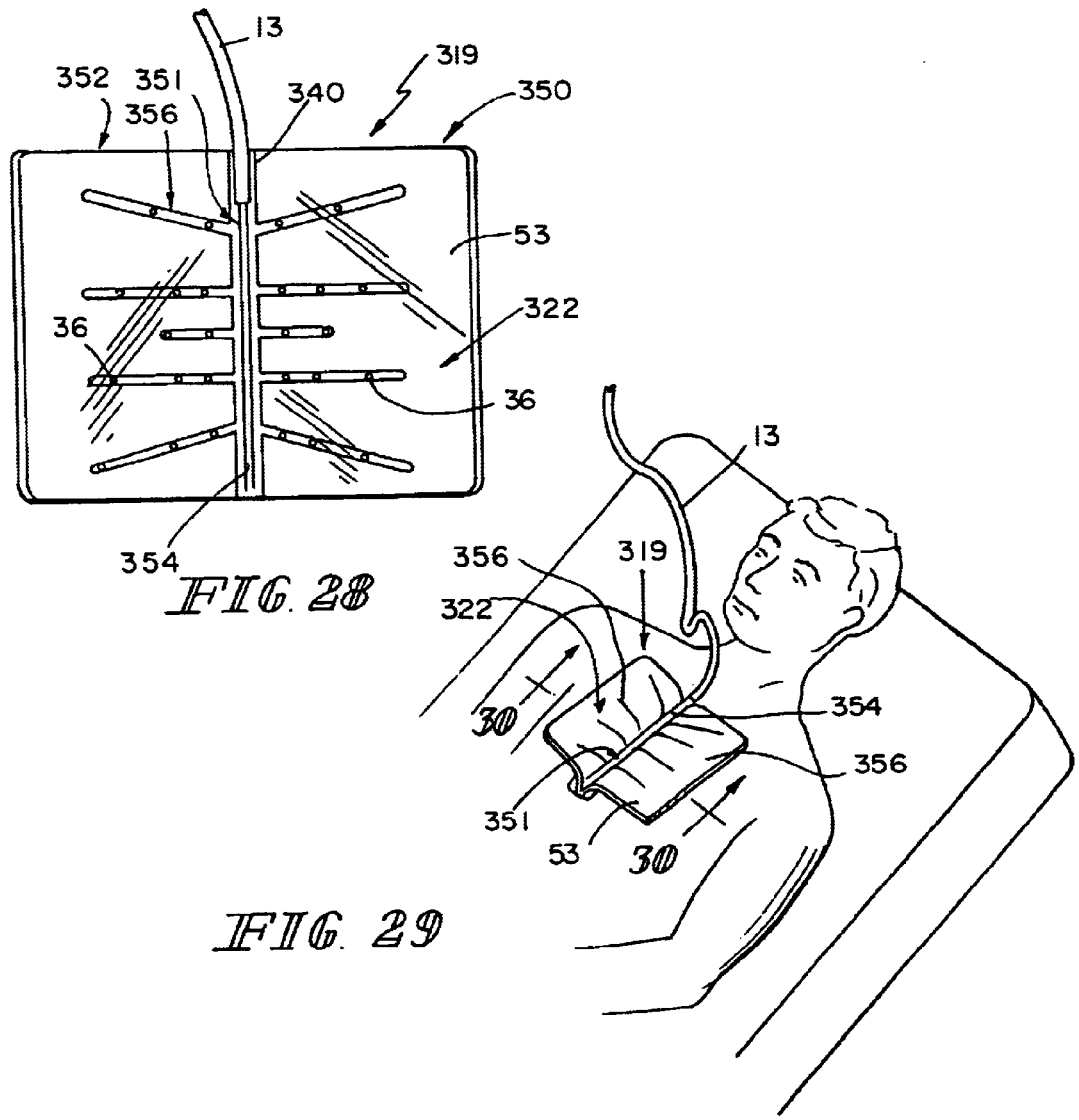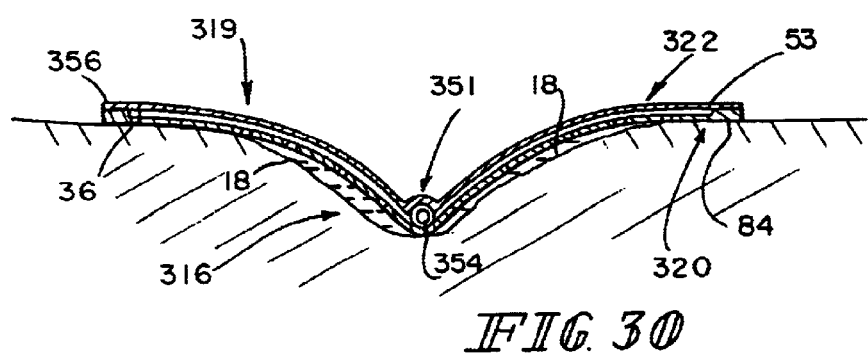

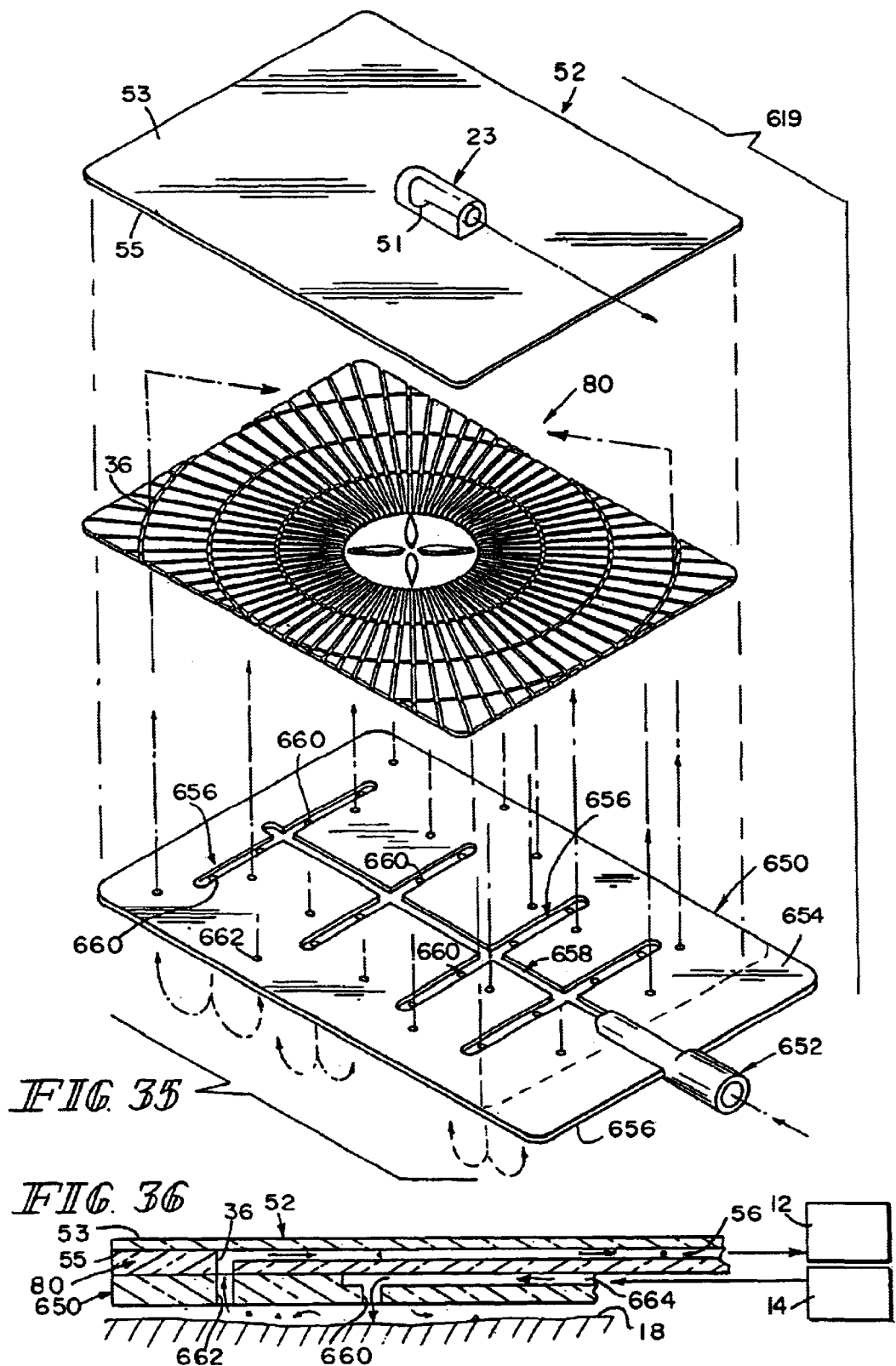

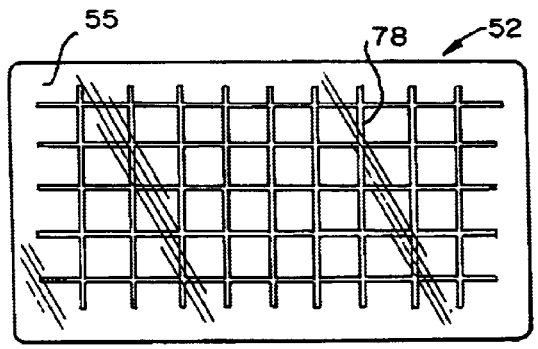
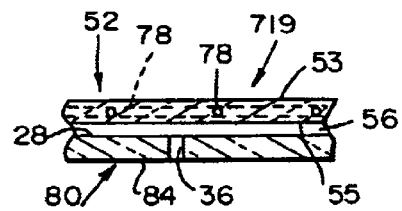
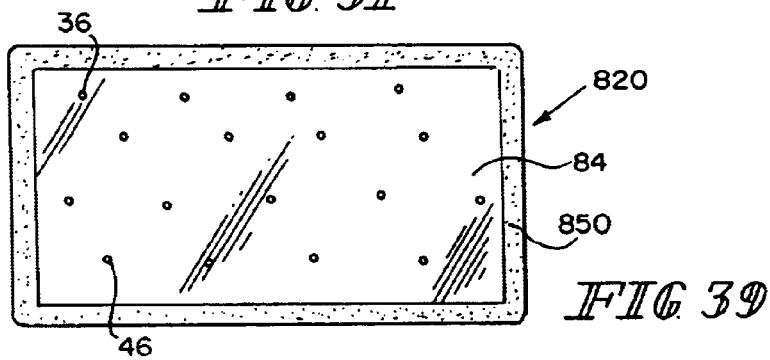
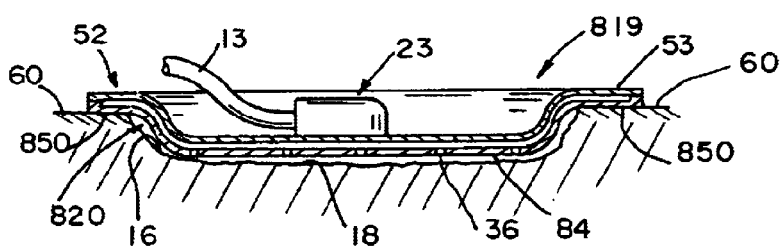

VACUUM THERAPY AND CLEANSING DRESSING FOR WOUNDS

This application is a Continuation-in-Part of application Ser. No. 09/725,352 filed Nov. 29, 2000 and titled "Vacuum Therapy and Cleansing Dressing for Wounds".

BACKGROUND AND SUMMARY OF THE INVENTION

The present invention relates to bandages for wounds, and more particularly to the provision of bandages for use with a vacuum source.

The prior art contemplates that chronic wounds may be treated by providing a vacuum in the space above the wound to promote healing. A number of prior art references teach the value of the vacuum bandage or the provision of the vacuum in the space above the surface of a chronic wound.

A vacuum bandage is a bandage having a cover which seals about the outer perimeter of the wound and under which a vacuum is established to act on the wound surface. This vacuum applied to the wound surface causes healing of chronic wounds. Typically, suction tubes are provided for drawing away exudate from the wound, and this suction may be used to create the vacuum under the cover. If the cover is a flexible cover, which is typically more comfortable for the patient, some sort of porous packing may be provided under the cover to provide the space in which the vacuum is formed. The following U.S. Patents establish the nature of vacuum treatment bandages and devices: U.S. Pat. Nos. 6,095,992, 6,080,189, 6,071,304, 5,645,081, 5,636,643, 5,358,494, 5,298,015, 4,969,880, 4,655,754, 4,569,674, 4,382,441, and 4,112,947. All of such references are incorporated herein by reference for purposes of disclosing the nature of such vacuum treatment of wounds.

As shown, for example, in U.S. Pat. No. 5,645,081 (hereinafter the '081 patent), a method of treating tissue damage is provided by applying negative pressure to a wound. The negative pressure is provided in sufficient duration and magnitude to promote tissue migration in order to facilitate the closure of the wound. FIG. 1 of the '081 patent discloses an open cell polyester foam section covering the wound, a flexible hollow tube inserted into the foam section at one end and attached to a vacuum pump at another end, an adhesive sheet overlying the foam section and tubing to adhere to the skin surrounding the wound in order to form a seal that allows the creation of a vacuum when the suction pump is operating. The '081 patent further teaches use of negative pressure between about 0.1 and 0.99 atmospheres, and that the pressure can be substantially continuous, wherein the pressure is relieved only to change the dressing on the wound. Alternatively, the '081 patent teaches use of a cyclic application of pressure in alternating periods of application and non-application. In a preferred embodiment, pressure is applied in 5 minute periods of application and non-application.

Various other prior art references teach the value of the vacuum bandage or the provision of vacuum to the surface of a chronic wound. Several Russian language articles exist which establish the efficacy of vacuum therapy discovered in the 1980's. Examples of such prior art articles, each of which discusses the use of application of vacuum to a wound to promote healing, are as follows: "Vacuum therapy in the treatment of acute suppurative diseases of soft tissues and suppurative wounds", Davydov, et al., Vestn, Khir., September 1988 (the September 1988 article); "Pathenogenic mechanism of the effect of vacuum therapy on the course of the wound process", Davydov, et al. Khirurigiia, June 1990 (the June 1990 article); and "Vacuum therapy in the treatment of suppurative lactation mastitis", Davydov, et al. Vestn. Khir., November 1986 (the November 1986 article).

The Russian articles distinguish wound drainage from the use of vacuum therapy for healing. The Russian authors report that vacuum therapy resulted in faster cleansing of the wound and more rapid detoxification than with the traditional incision-drainage method. The November 1986 Russian article describes the vacuum therapy techniques as a reduction of 0.8–1 atmosphere for 20 minutes at the time of surgery, and subsequent 1.5 to 3 hour treatments at a reduced pressure of 0.1 to 0.15 from atmosphere, twice daily. These Russian articles teach the use of negative pressure to effect healing. The articles describe using several sessions per day, each lasting up to one hour, with a vacuum of 76–114 mmHg. The Russian articles teach using this vacuum method to decrease the number of microbes in the wound. The June 1990 article teaches that this vacuum therapy provides a significant antibacterial effect. The article describes the stepped up inflow of blood to the zone around the wound to lead to an increase in the number of leukocytes reaching the focus of inflamation. Subsequent articles and patents further develop the benefits obtained with vacuum therapy. The prior art, therefore, teaches the benefit and value of a vacuum bandage.

According to the present disclosure, a thin, flexible member for use in a vacuum bandage is provided. The member includes a wound contacting surface configured to be in contact with and conform to a wound surface of a wound. The member further includes a plurality of discrete holes formed in the wound contacting surface, a port which communicates with the vacuum source, and communicating means between the holes and the port. The member is made from a generally noncompressible material. Further, the material is generally transparent and non-porous.

In some illustrative embodiments, the communicating means comprises a plurality of distinct passageways between each hole and the port. The member includes a wound contacting layer having channels formed therein and a cover coupled to the wound contacting layer. The cover cooperates with the wound contacting layer, and the channels formed therein, to define the passageways. The member further includes a boss positioned near the port of the cover to prevent an upper surface of the wound contacting layer from sealing off the port of the cover when vacuum is applied to the port.

In some illustrative embodiments, the wound contacting surface of the member includes spacers contacting the wound to define a suction space between the member and the wound surface. The wound contacting surface may also be textured or roughened for contact with the wound surface. The unevenness of the textured or roughened surface provides communication of the negative pressure across the wound surface.

In some embodiments, the spacers and suction space are defined by a plurality of channels formed in the wound contacting surface. Each of the channels formed in the wound contacting surface opens toward the wound surface and includes side edges contacting the wound.

In some embodiments of the invention, the dressing member has such a plurality of channels formed in patterns on both of the wound contacting surface and the opposite surface and the plurality of holes provide communication between the channels on both surfaces. In some embodiments, the channel patterns on both surfaces are congruent or superimposed with both patterns radiating outwardly from the port and with the holes spaced radially along the channels.

In some embodiments, the dressing member is made from a material which is to be trimmed conformingly to fit the wound. In some embodiments, the dressing member is relatively transparent such that the condition of the wound surface can be observed through the wound member.

There is provided, therefore, a dressing for a wound, the dressing comprising a relatively thin flexible member which can be trimmed conformingly to fit the wound surface. A suction and irrigation port is associated with the dressing member, and a plurality of channels or passageways is formed in the member leading away from the port to provide communication between the port and areas of the wound surface. The dressing member is provided with a plurality of through holes in communication with the channels. A packing may be placed over the flexible member and a sealing film may be placed over the packing to seal around the perimeter of the wound to provide an enclosed space above the member in which a vacuum is formed by suction on the port. It will be appreciated, however, that some caregivers may choose to leave packing out of the bandage and have the sealing film placed directly over the flexible member. It has been found that some bandages function quite well without packing. Also, visual observation is improved without the packing. Irrigation fluid may be introduced to the port to impinge upon the wound surface and this fluid and wound exudate is removed from the space between the wound and the bandage member by suction applied to the port. It will be appreciated that the vacuum therapy and the irrigation therapy may take place without removal of the bandage. The illustrative member with the downwardly opening channels or spacers on the wound contacting surfaces provides a suction space which will uniformly apply the vacuum and the irrigation to the surface of the wound bed.

The covered channels on the opposite surface and the holes through the member further contribute to the ability to uniformly apply the vacuum therapy and irrigation fluid to the wound surface. A relatively large portion of the wound surface will be exposed to the vacuum therapy and irrigation using the illustrative bandage member. A large number of redundant passageways are provided for communicating from the access port directly to the wound surface. While some of the passageways may become blocked by exudate particles from the wound surface, other passageways will remain open for suction and irrigation.

The illustrative bandage, therefore, provides a relatively thin, flexible, comfortable bandage member which can be trimmed generally conformingly to fit into a wound bed and apply vacuum therapy and irrigation uniformly to the wound surface. The illustrative covered channel passageways on the opposite (upper or outer) surface provide a multitude of clearly defined passageways leading from the access port to the through holes leading directly into the suction space under the member.

In further embodiments, the member includes a connecter coupled to the cover for communication with the port of the cover. The connecter is configured for communication with the vacuum source and defines a right-angled passageway to provide a horizontal tube attachment.

In yet another embodiment, the member further includes an outer adhesive perimeter. This perimeter is configured to seal about the wound to a patient's healthy skin surrounding the wound. In another embodiment, the member further includes a wire form to permit a user or caregiver to mold or shape the member to fit the particular shape of a wound. In one embodiment, the wire form is molded into the cover and in another embodiment the wire form is molded into the wound contacting layer.

In still another embodiment, the member further includes a plurality of irrigation passageways configured for communication with an irrigation source and with the wound surface. The irrigation passageways are distinct from the passageways described above which are configured for communication with the vacuum source. The member further includes an irrigation port in communication with the irrigation passageways and configured for communication with the irrigation source. An irrigation layer is provided and includes channels formed therein which define the irrigation passageways.

A wound bandage for use on a chronic wound located on a patient's heel is also disclosed. In this embodiment, the member is saddle-shaped and includes an upper portion, a lower portion, and a neck portion coupled to and positioned between the upper portion and the lower portion. The saddle-shaped member is foldable into a configuration that cups the patient's heel. An embodiment having a member with a generally "V-shaped" cross-section is provided for use with sternal or abdominal wounds. The V-shaped member includes a right wing and a left wing coupled to the right wing. Further, the V-shaped member includes a central passageway in communication with the port of the cover and a plurality of lateral passageways in communication with the central passageway.

Another alternative member is disclosed for use with tunneled wounds. This member includes a truncated cone-shaped portion, a tube-shaped portion coupled to the cone-shaped portion, and a dome-shaped portion coupled to the tube-shaped portion. The port is positioned in the cone-shaped portion. Yet another member is disclosed which is dome-shaped and has a convex wound contacting surface.

A method of forming a member of a wound bandage is further provided in accordance with the present disclosure. The method includes the steps of molding a cover from a semi-cured silicone and the step of heat-sealing the cover to a wound contacting layer. In illustrative embodiments, the method further includes providing a connecter and heat sealing the connecter to the cover. In further embodiments, the method includes molding the connecter and the wound contacting layer from fully-cured silicone.

Additionally, a method of treating an open wound having a wound surface is provided in accordance with the present disclosure. The method includes the steps of providing a flexible member fabricated from non-porous material to have a wound contacting surface with holes in the surface, a port configured to communicate with a vacuum source, and passageways providing communication between the holes and the port. The method further includes placing the member into contact with the wound to functionally and physically interface with the wound surface and connecting the port to a vacuum source to provide suction at each of the holes. In illustrative embodiments, the method further includes the step of covering the wound and the member adjacent the wound to provide a space in which a vacuum is established by the vacuum source. In other embodiments, the method includes the step of irrigating the wound surface by connecting the port to a source of irrigation fluid expelled through the holes onto the wound surface.

Features of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 7 is a sectional view of the bandage within the wound of the patient showing the wound surface, the wound contacting surface of the member adjacent the wound surface, the cover adjacent the opposite surface of the member, the tubing coupled to the port of the member, packing, and the outer film coupled to the patient's healthy skin to seal the environment;

FIG. 8 is another embodiment showing an alternate wound contacting surface of the member including spacers for contacting the wound surface to form an open space between the member and the wound surface;

FIG. 9 is a sectional view taken along line 9—9 of FIG. 8 showing one spacer and a through hole of the alternate member;

FIG. 10 is another embodiment showing an another wound contacting surface of the member including spacers or oblong ridges provided to form an open space between the member and the wound surface when the member is placed in the wound;

FIG. 11 is a sectional view taken along line 11—11 of FIG. 10 showing one oblong ridge and through hole of the alternate member;

FIG. 12 is another embodiment showing a wound care bandage having two ports;

FIG. 13 is another embodiment showing an alternate opposite surface of the member having ridges radially spaced around the port to provide a means of flow for exudate being vacuumed from the wound and/or for liquid being dispensed to the wound through the port;

FIG. 14 is a sectional view taken along line 14—14 of FIG. 13;

FIG. 15 is yet another embodiment showing a bandage having a plurality of ports each coupled to a vacuum/irrigation tube to provide an evenly distributed suction force across the member;

FIG. 26 is a perspective view of another embodiment of the member showing the member having a truncated cone-shaped portion coupled to a tube-shaped portion for use with tunneled wounds, as shown in FIG. 27;

FIG. 27 is a sectional view of the member shown in FIG. 26 showing the member positioned within the tunneled wound of a patient;

FIG. 28 is a top view of a "V-shaped" member for use with sternal or abdominal wounds, for example;

FIG. 29 is a perspective view of the V-shaped member of FIG. 28 showing the member on the sternal wound of a patient;

FIG. 30 is a sectional view taken along line 30—30 of FIG. 29 showing the V-shape of the member and also showing the wound contacting surface of the member adjacent the sternal wound surface;

FIG. 35 is an exploded perspective view of another member showing the member including a cover, a wound contacting irrigation layer, and an intermediate layer positioned between the cover and the irrigation layer;

FIG. 36 is a sectional view of the member of FIG. 35 showing the irrigation layer in communication with an irrigation source (illustrated diagrammatically) and showing the cover in communication with a vacuum source (illustrated diagrammatically) to provide the member with the capability to simultaneously apply vacuum and irrigate the wound;

FIG. 37 is a bottom view of a cover showing a filament or wire form molded into the cover to allow the member to retain a desired shape when shaped or formed by a user or caregiver to fit a particular wound, for example;

FIG. 38 is a sectional view of a member including the cover and wire form shown in FIG. 37;

FIG. 39 is a bottom view of another member showing the wound contacting layer having an adhesive outer perimeter for sealing about the wound in order to provide a self-sealing member, as shown in FIG. 40;

FIG. 40 is a sectional view of the member of FIG. 39 showing the outer adhesive perimeter of the wound contacting layer coupled to the patient's healthy skin surrounding the wound in order to seal the member about the wound without the use of the sealing film shown in FIG. 17.

DETAILED DESCRIPTION OF THE DRAWINGS

Figure 1:
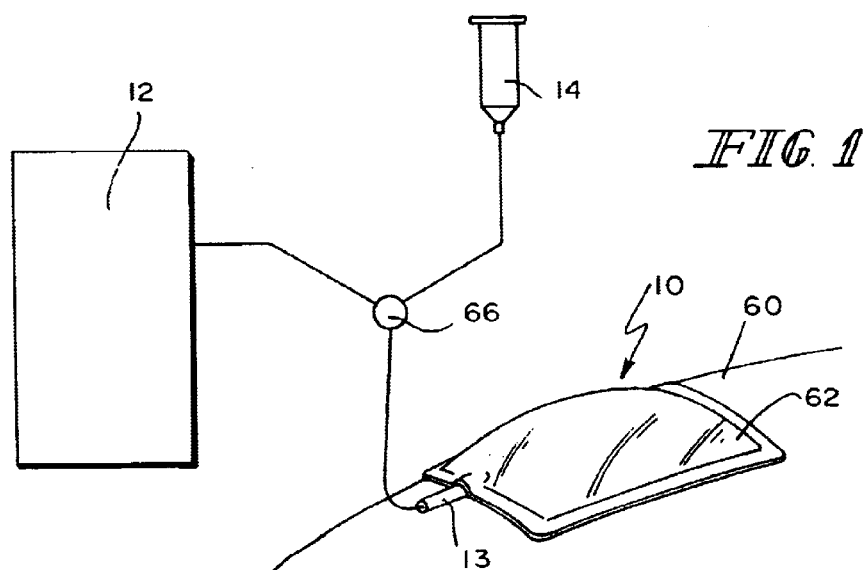
FIG. 1 is a part perspective, part diagrammatic view of a wound care bandage showing the wound care bandage located on the leg of a patient and coupled to both a vacuum and an irrigation source through the use of a switch valve.

A wound care bandage 10 is provided for use with a vacuum and irrigation source 12, 14, respectively, as shown in FIG. 1. An illustrative vacuum and irrigation source 12, 14 is disclosed in application Ser. No. 09/725,666 filed on Nov. 29, 2000 and application Ser. No. 09/369,113 filed Aug. 5, 1999. These pending applications, which are each owned by the assignee of this present application, are specifically incorporated herein by reference.

Bandage 10 promotes the healing of a large wound 16 (shown in FIGS. 3 and 7) by providing vacuum therapy to the wound 16 to promote blood flow and remove exudate from a wound surface 18 of the wound 16 and by providing for irrigation of the wound 16 with fluids such as saline, for example.

Figure 2:
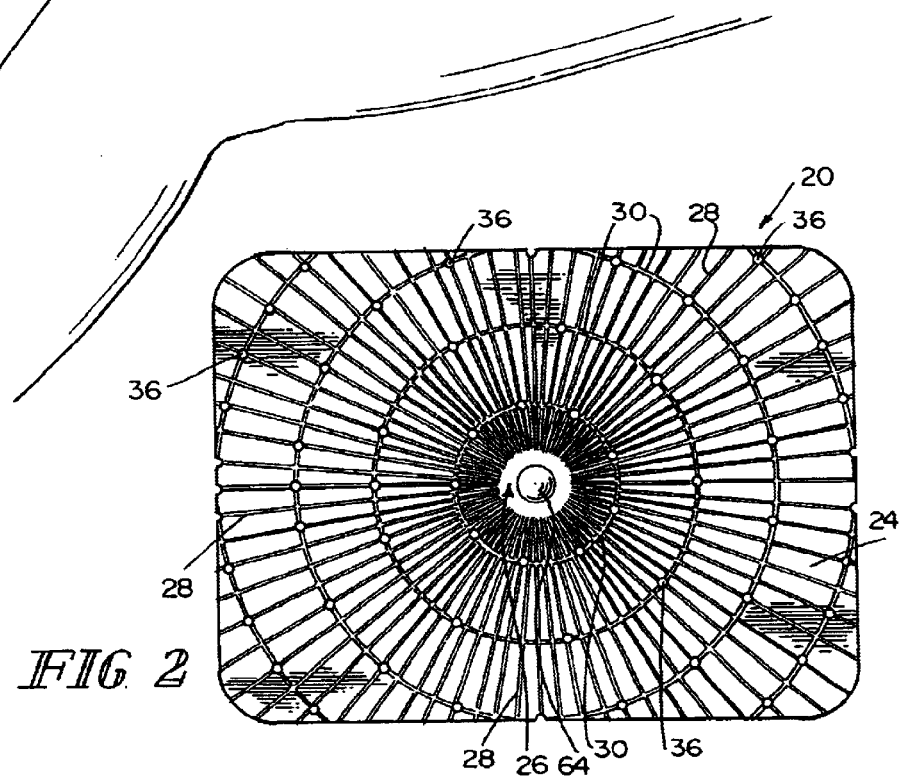
FIG. 2 is a top view of a member of the wound care bandage showing the member including a vacuum/irrigation port, a plurality of channels radiating outwardly from the port, and through holes which extend through the member.
Figure 3:
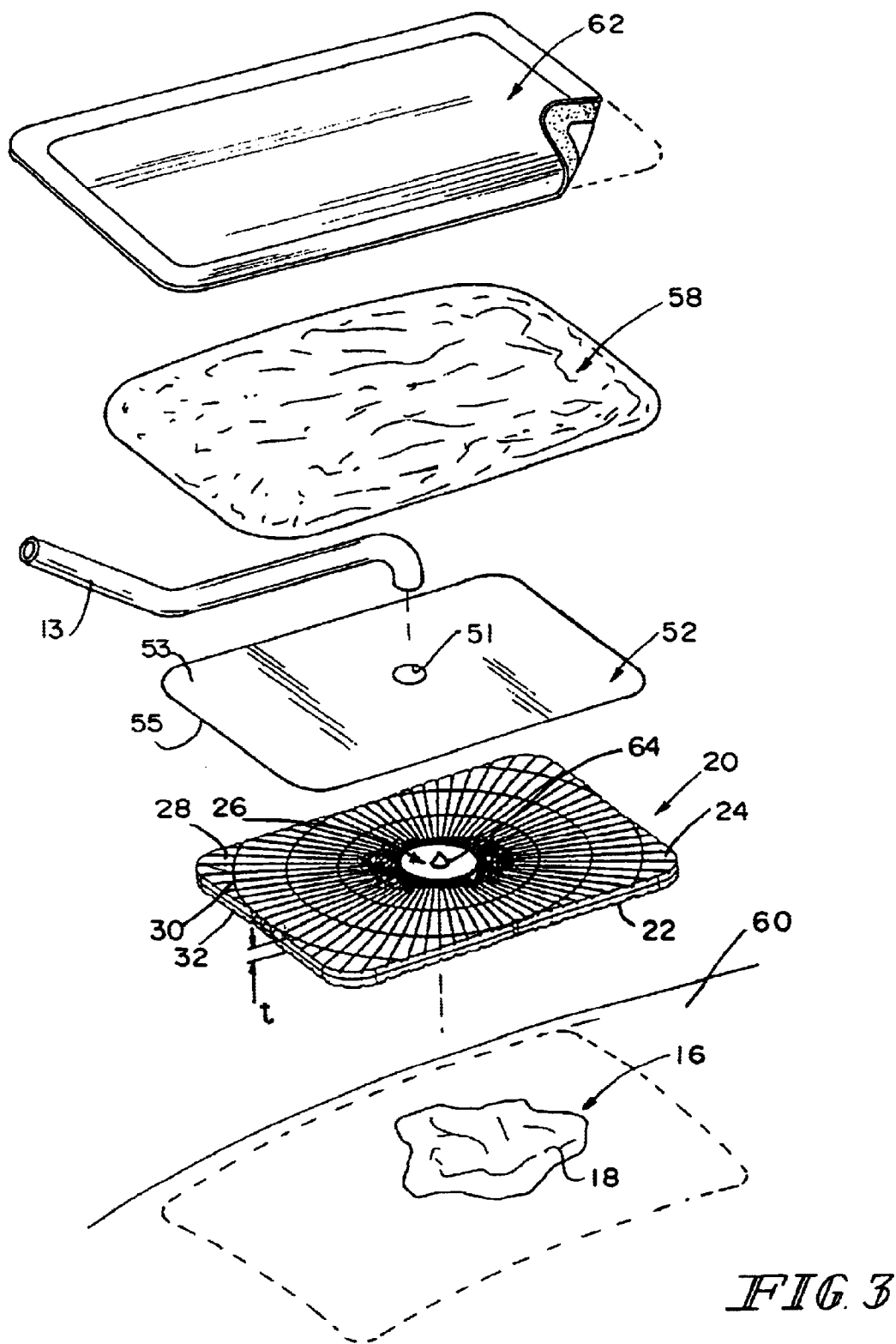
FIG. 3 is an exploded view of one embodiment of the wound care bandage showing the member having a wound contacting surface and an opposite surface, a cover adjacent the opposite surface, tubing which connects to the port of the member at one end and to the vacuum and irrigation sources at another end, packing to be placed on top of the tubing and member, and a sealing film which closes and seals the bandage to allow a vacuum environment to be created.

As shown in FIG. 3, wound care bandage 10 comprises a thin, flexible wound dressing member 20, shown in FIG. 2. Member 20 is made of a medical grade silicone or other type of elastomer which is pliable. Two companies, for example, which manufacture such medical grade silicone are GE Silicones and NuSil Technology. It is within the scope of this disclosure, however, to include a wound dressing member made of any type of thin, flexible material that is non-porous and non-foam-like. This thin, flexible material is also generally non-absorptive. For example, materials such as polyvinylchloride (PVC), PVC free of diethylhexyl phthalate (DEHP-free PVC), polyurethane, or polyethylene may be used in the manufacture of member 20.

Further, member 20 may be molded to include anti-microbial constituents. For example, it is within the scope of this disclosure to impregnate member 20 with silver ions which are known anti-microbials. The following PCT publications illustrate the use of anti-microbials in various products and are incorporated herein by reference: "Antimicrobial Plastic Closures for Drinking Containers", WO 00/26100; "Antimicrobial Contact Lens Case", WO 00/038552; "Antimicrobial Fabric and Medical Graft of the Fabric", WO 00/32247; "Antimicrobial Suturing Ring for Heart Valve", WO 00/30567.

Member 20 is also made of a generally non-adhesive material. Therefore, wound contacting layer 22, which lies adjacent to the wound surface 18, does not adhere to the wound surface 18. Further, member 20 is solid in nature and generally non-compressible. For example, when a negative pressure is applied to member 20, a thickness, t, of member 20, as shown in FIG. 3, remains relatively constant.

Figure 4:
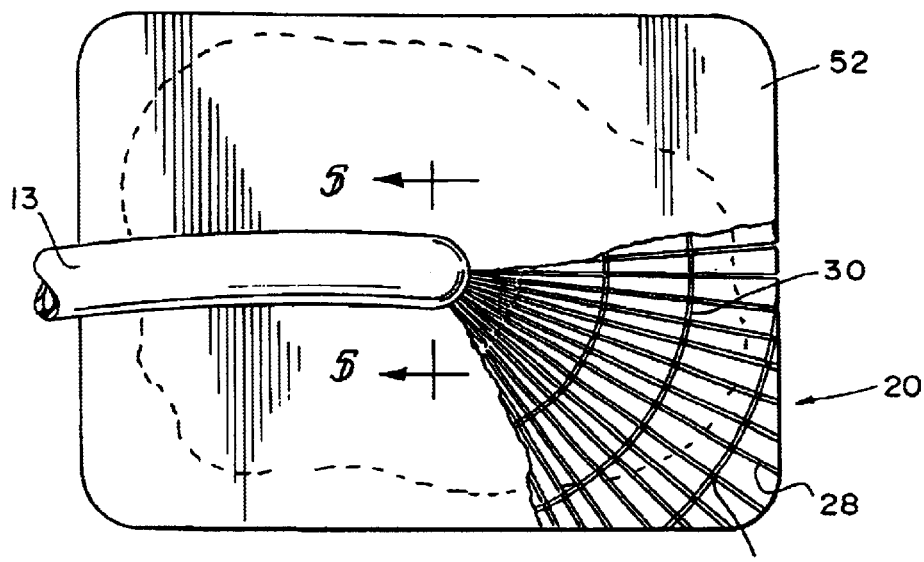
FIG. 4 is a top view of a portion of the bandage showing the cover with portions broken away and showing the member and the channels of the member enclosed by the cover in order to form passageways extending away from the port.
Figure 6:
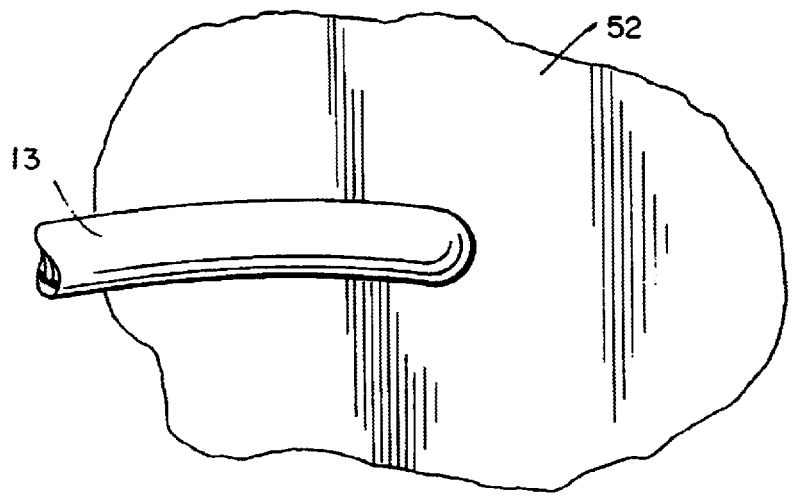
FIG. 6 is a top view of the portion of the member and cover shown in FIGS. 4 and 5 after having been trimmed to fit the particular wound of the patient.

As shown in FIG. 2, wound dressing member 20 is illustratively rectangular in shape. However, it is within the scope of the this disclosure for member 20 to be any suitable shape, some illustrative examples of which are described below in FIGS. 23–31. Further, member 20 may be cut to fit any size wound 16, as shown in FIGS. 4 and 6. Member 20 is illustratively molded with a thickness of 0.080 inches (2.032 mm). Illustratively, member 20 is made from a silicone of a Durometer 50A which is flexible. It will be appreciated that the channels or passageways formed in the member, as described below, will further contribute to its flexibility.

Figure 5:
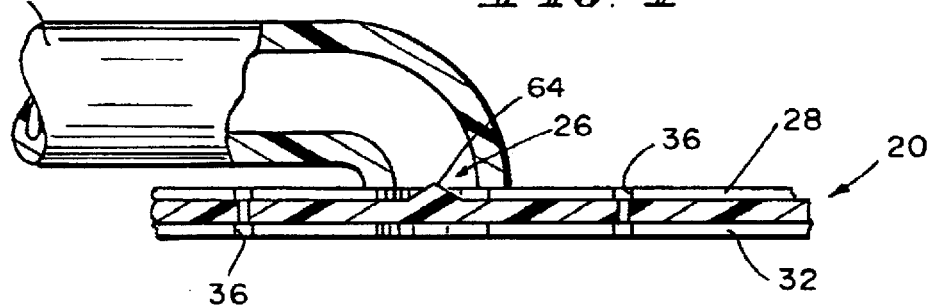
FIG. 5 is a sectional view taken along line 5—5 of FIG. 4 showing the tube which may be sealed to the port, showing a shallow cone of the port, and also showing the channels of the opposite surface and channels of the wound contacting surface and the holes which communicate between the channels.
Figure 16:
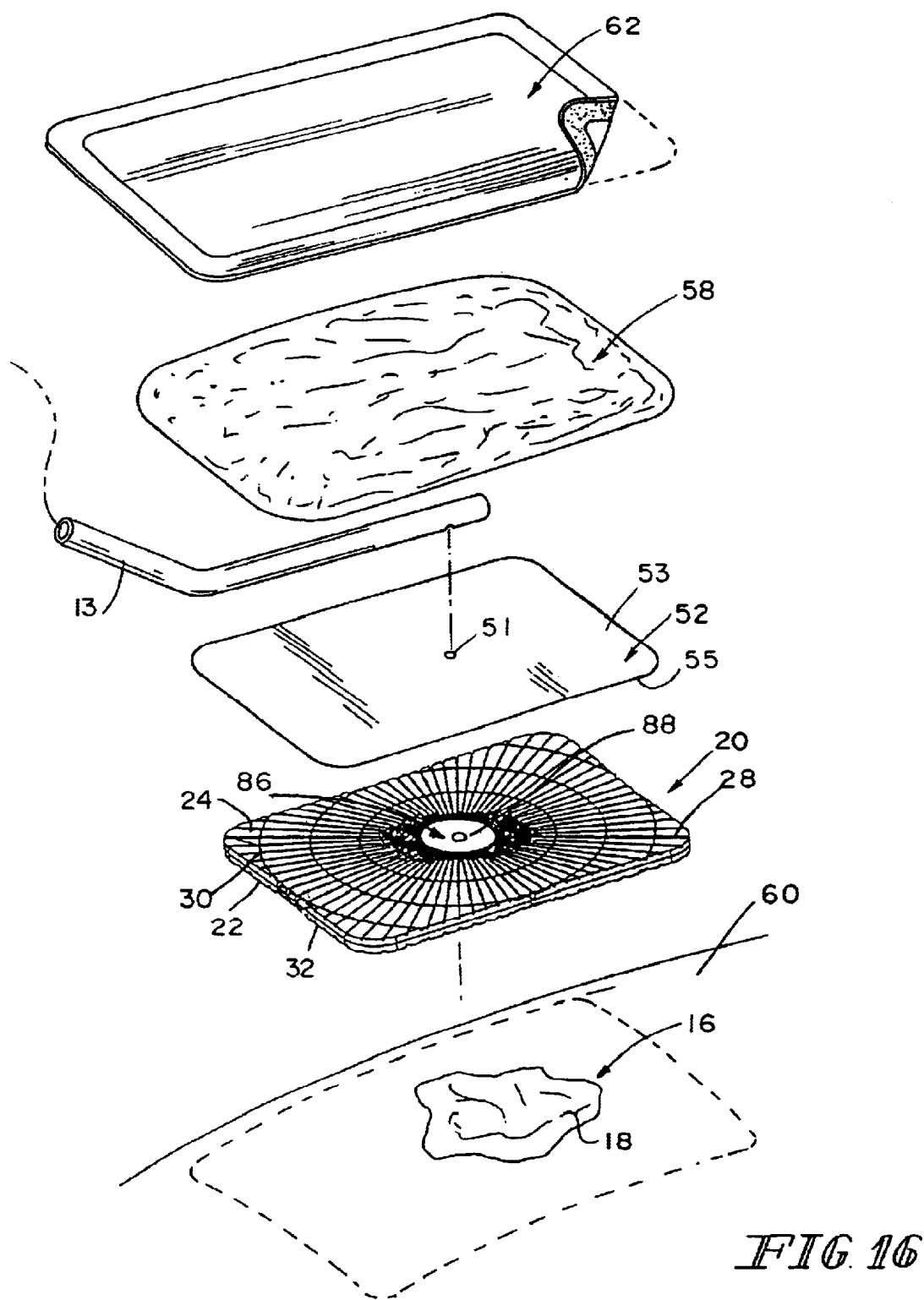
FIG. 16 is another embodiment showing a member of the bandage having a central aperture at the port of the member and channels extending radially outwardly from the central aperture.

Member 20 includes a wound contacting surface 22 and an opposite surface 24. Wound contacting surface 22 or portions thereof contact the wound surface 18 as shown in FIG. 7. Looking to FIG. 2, it can be seen that opposite surface 24 includes a central area defining a vacuum/irrigation port 26. A plurality of channels 28 are formed in opposite surface 24 and extend radially away from central area or port 26. Illustratively, each channel 28 is 0.030 inches (0.762 mm) wide and 0.030 inches (0.762 mm) deep. It is within the scope of this disclosure, however, to include channels 28 of member 20 having various widths and depths suitable for the present application. Port 26, as shown in FIG. 5, includes a shallow cone 64 in order to induce fluids dispensed through a vacuum/irrigation tube 13 from the vacuum and irrigation sources 12, 14 to flow evenly into channels 28. In an alternate embodiment shown in FIG. 16, an alternate port 86 includes an aperture 88 formed through member 20. In the FIG. 16 embodiment, the port communicates directly with the suction/irrigation space between the member 20 and the surface of the wound.

Vacuum/irrigation tube 13 is in communication with central area or port 26 of member 20 via a port 51 of a cover 52 (described below) of the bandage 10. coupled to the port. The tube 13 may be molded as part of the member 20 or attached to the member by welding, adhesion or other known techniques. The tube is preferably made of silicone, however, it is within the scope of this disclosure to include a vacuum/irrigation tube made of other medically suited materials. Opposite surface 24 further includes channels 30 which are concentric with port 26, as shown in FIG. 2. Concentric channels 30 have the same width and depth as that of channels 28 described above.

Wound contacting surface 22 includes a plurality of channels 32 which radiate outwardly from the center of member 20 similar to channels 28 of opposite surface 24. Similarly, wound contacting surface 22 also includes a plurality of channels 34 concentric with the center of member 20. Each channel 32, 34 of wound contacting surface 22 opens toward the wound surface 18 and includes outer edges 42 which contact the wound surface 18 or which act as spacers to provide space between the member 20 and the wound surface. Illustratively, the channels 32, 34 of wound contacting surface 22 have the same dimensions as the channels 28, 30 of opposite surface 24. In other words, illustratively channels 32, 34 of wound contacting surface 22 are 0.030 inches (0.762 mm) deep and 0.030 inches (0.762 mm) wide. However, it is within the scope of this disclosure to include channels 32, 34 of surface 22 having other widths and depths.

Through holes 36 are provided in member 20 for communication between the channels 28, 30 of the opposite surface 24 with the channels 32, 34 of the wound contacting surface 22. As shown in FIG. 2, holes 36 are illustratively positioned to lie within concentric channels 30, 34 of each respective surface 22, 24 of member 20. Holes 36 are illustratively 0.020 inches (0.508 mm) in diameter and are illustratively spaced approximately 0.500 inches (12.700 mm) apart along channels 28, 30, and 32, 34 of each respective surface 22, 24. It is, however, within the scope of the disclosure to include holes having other suitable size diameters and other spacing.

Channels 32, 34 of wound contacting surface 22 provide open spaces 40 between the wound surface 18 and member 20, as shown in FIG. 7. Open spaces 40 are defined by each channel 32, 34 of wound contacting surface 22, each outer edge 42 of channels 32, 34, and wound surface 18. Each through hole 36 of member 20 opens into the open spaces 40 formed by channels 32, 34. Open spaces 40 allow vacuum source 12 to establish a generally uniformly distributed vacuum therapy to draw exudate from the wound 16 into the channels 32, 34 of wound contacting surface 22.

It is within the scope of this disclosure to provide spacers 46, for example, shown in FIGS. 8 and 9. Spacers 46 protrude outwardly from wound contacting surface 22 to contact wound surface 18. Open spaces 40 are provided between spacers 46. As shown in FIG. 9, each spacer 46 has an illustrative depth of approximately 0.030 inches (0.762 mm). However it is within the scope of this disclosure to include spacers having other suitable dimensions which provide open spaces 40. As with member 20 including channels 32, 34 on wound contacting surface 22, holes 36 of member 20 including spacers 46 are positioned to open into the open spaces 40.

Further, it is within the scope of this disclosure to include member 20 having other types of spacers on wound contacting surface 22 which creates open spaces 40 when wound contacting surface 22 is adjacent the wound surface 18. In another embodiment, as shown in FIGS. 10 and 11, oblong ridges 50 are provided on wound contacting surface 22. Ridges 50 are similar in shape and function to spacers 46. Ridges 50 protrude away from member 20 and contact wound surface 18 when member 20 is place on wound surface 18 to provide open spaces 40 between wound surface 18 and member 20 to establish a generally uniform vacuum across the wound surface 18. As shown in FIG. 11, each ridge 50 illustratively has a preferred depth of 0.030 inches (0.762 mm), however, a ridge having other suitable dimensions is within the scope of this disclosure. As illustrated by channels 32, 34 of wound contacting surface 22, spacers 46, or ridges 50, it is within this disclosure to include other structures which acts as spacers to create open spaces 40 between the wound surface 18 and member 20 when member 20 is placed on the wound surface 18 to distribute suction and irrigation generally uniformly throughout the wound 16. For example, the wound contacting surface maybe textured or roughened as illustrated by irregular nubs 74 in FIGS. 21 and 22. This textured surface is described in more detail below with respect to a bandage 11 shown in FIG. 17.

As mentioned above, bandage 10 further comprises cover 52 for covering and coupling to opposite surface 24 of member 20. Port 51 of cover 52 communicates with central area or port 26 of member 20 and channels 28 of member 20. Cover 52 is provided to cover channels 28, 30 of opposite surface 24. Cover 52 and channels 28 of opposite surface 24 cooperate to form passageways 56, as shown in FIG. 7, extending away from port 26. Passageways 56 are also formed by the cooperation of concentric channels 30 of opposite surface 24 and cover 52. Cover 52 is adhered to member 20 through the use of an adhesive or other suitable means such as heat sealing, for example, which is described in more detail below. It will be appreciated that the covered channels 28, 30 provide an ideal way to fabricate a multitude of passageways 56 communicating with the wound surface. In an alternate embodiment, passageways 56 are formed by cooperation of ridges 54 on opposite surface 24 of member 20, rather than channels 30, and cover 52, as shown in FIGS. 13 and 14, for example. It is within the scope of this disclosure to include a bandage 10 forming other passageways 56 extending away from port 26. Holes 36 of member 20 having ridges 54 are located within passageways 56 of bandage 10 similar to holes 36 of member 20 having radial channels 28 and concentric channels 30.

It will be appreciated that the illustrative cover 52 may be provided with scale marking for gauging the wound size or healing progress. Circular markings may be added at 0.5 cm or 1.0 cm intervals, for example, to provide convenient measuring of the wound and healing progress.

As shown in FIGS. 3 and 7, bandage 10 further includes gauze or other suitable packing 58 which lies on top of cover 52 and is provided to fill the wound 16 up to the surface of the patient's healthy skin 60. As noted above, such packing 58 may be optional with the caregiver. A sealing film 62 of bandage 10 is placed over packing 58. Film 62 is provided to cover the entire wound 16 and to extend across and attach around tube 13 to the patient's healthy skin 60, as shown in FIGS. 1 and 7. Preferably, film 62 is an occlusive or semi-occlusive material which allows water vapor to permeate through. Because of this characteristic, the film 62 is referred to as Moisture Vapor Transmission Rate film or MVTR film. The products Tegaderm™, made by 3M, and OpSite™ made by Smith and Nephew can be used for film 62, for example. The product OpSite™ is a semi-permeable film. Film 62 is approximately 0.003 inches (0.076 mm) thick, however, it is within the scope of this disclosure to include any occlusive or semi-occlusive film 62 having other thickness. Film 62 is provided to create a sealed environment below the film 62 and around the wound 16 in which a vacuum or negative pressure can be maintained as provided by vacuum source 12.

As shown in FIG. 7, vacuum/irrigation tube 13 or an extension added to the tube 13 extends over the edge of member 20 and cover 52 and out from under the edge of the sealing film 62. In use, irrigation source 14 delivers liquid through tube 13 and port 51 of cover 52 to port 26 and onto the top of a shallow cone 64 of member 20 which extends upwardly as shown in FIGS. 5 and 7. Cone 64 acts to spread the liquid out through the passageways 56 formed by the cooperation of channels 28, 30 (or ridges 54) and cover 52. The fluid moves radially out through passageways 56 to holes 36. The fluid then moved down through holes 36 to open spaces 40 to impinge on wound surface 18.

A switch valve 66 is illustratively provided, as shown in FIG. 1, to allow a user to switch between the use of the vacuum source 12 and the irrigation source 14. It will be appreciated that mechanism other than the switch valve 66 may be used selectively to couple the vacuum source or the irrigation source to the bandage. Simple tube clamps, for example, may be used selectively to open and close the tube set provided with the bandage 10. When valve 66 is switched to operate the vacuum source 12, the vacuum suction draws exudate into the open spaces 40 and up through the holes 36. The exudate is then drawn radially inwardly through passageways 56 toward port 26 and finally through tube 13.

Although illustrative bandage 10 includes one central port 51 of cover 52 and central area or port 26 of member 20, it is within the scope of this disclosure to include multiple ports 70, as shown in FIGS. 12 and 15, for example. Bandage 10 may make use of two ports 70 located at opposite ends of member 20, as shown in FIG. 12. Alternately, as shown in FIG. 15, bandage 10 may make use of a plurality of ports 70 spaced throughout member 20. It is contemplated that, in some embodiments having two ports, one port may be used for suction or vacuum therapy and the other port may be used for irrigation therapy.

It is contemplated that irrigation source 14 may be operated to provide irrigation fluid at various selected pressures. It is also contemplated that the bandage 10 and dressing member 20 may be provided in various sizes and shapes, some examples of which are shown in FIGS. 23–31 and are discussed below. The dressing member 20 may be reused with a single patient. It is also contemplated that the dressing 10 may be used with manual irrigation (where a nurse uses the syringe manually) as well as the powered syringe 14.

Referring now to FIGS. 17–22, there is shown another exemplary embodiment of a wound care bandage 11. Bandage 11 is somewhat similar to bandage 10. As such, the same reference numerals have been used to designate similar components to those components previously discussed in regard to FIGS. 1–7, and additional discussion thereof is not warranted. One difference between bandage 10 and bandage 11 is that a wound dressing member 19 of FIGS. 17–22 is defined as including the combination of a wound contacting layer 80, similar to member 20 of FIGS. 1–7, cover 52 coupled to layer 80, and a connecter 23 coupled to cover 52 for communication with vacuum source 12 and/or irrigation source 14. It is also within the scope of this disclosure for connecter 23 to be integrally coupled to cover 52.

Similar to member 20, member 19 is thin and flexible. Layer 80, cover 52, and connecter 23 are each made of a medical grade silicone or other type of pliable elastomer as described above with respect to member 20. Member 19 is similarly non-porous, non-foam-like, and generally non-absorptive. Materials such as PVC, DEHP-free PVC, polyurethane, or polyethylene may similarly be used in the manufacture of member 19. Further, layer 80, cover 52, and connecter 23 of member 19 may each be molded to include anti-microbial constituents similar to member 20.

Figure 18:
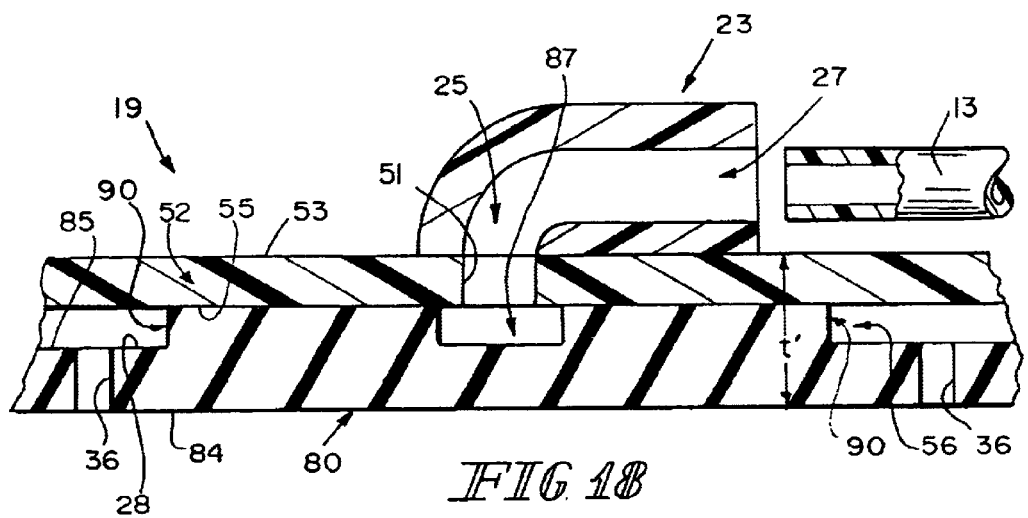
FIG. 18 is a sectional view of the member of FIG. 17 showing the non-porous nature of the member and also showing distinct passageways and through holes of the member.
Figure 19:
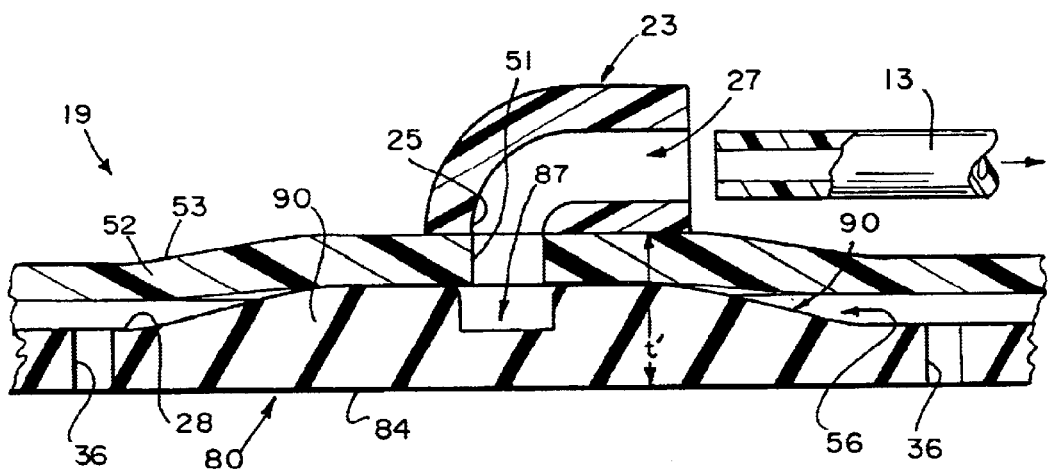
FIG. 19 is a sectional view similar to FIG. 18 showing rounded protrusions or bosses of the wound contacting layer adjacent to the cover and positioned about a port of the cover.
Figure 20:
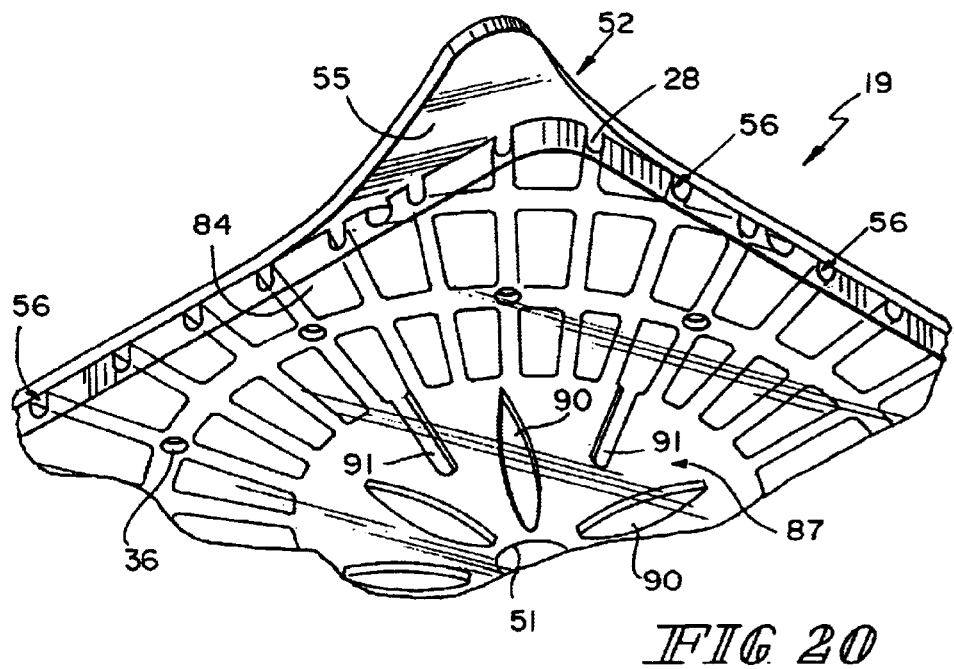
FIG. 20 is a bottom perspective view of the member showing a smooth wound contacting surface of the member and also showing the transparent nature of the member.

Also similar to member 20, member 19 is made of a generally nonadhesive material to prevent wound contacting layer 80, which lies adjacent to the wound surface 18, from adhering to the wound surface 18. Further, member 19 is similarly solid in nature and generally non-compressible. For example, when a negative pressure is applied to member 19, a thickness t', of member 19, as shown in FIGS. 18 and 19, remains relatively constant. Thickness, t', represents solid areas of member 19 where a channel or passageway is not present. Member 19 is generally pliable and flexible, but is not generally compressible. Further, as shown in FIG. 20, member 19 (like member 20) is transparent to enable a caregiver to be able to see the wound 16 through member 19 when member 19 is placed adjacent to wound surface 18. This transparency allows the caregiver to view the progress of the healing of the wound 16.

Figure 17:
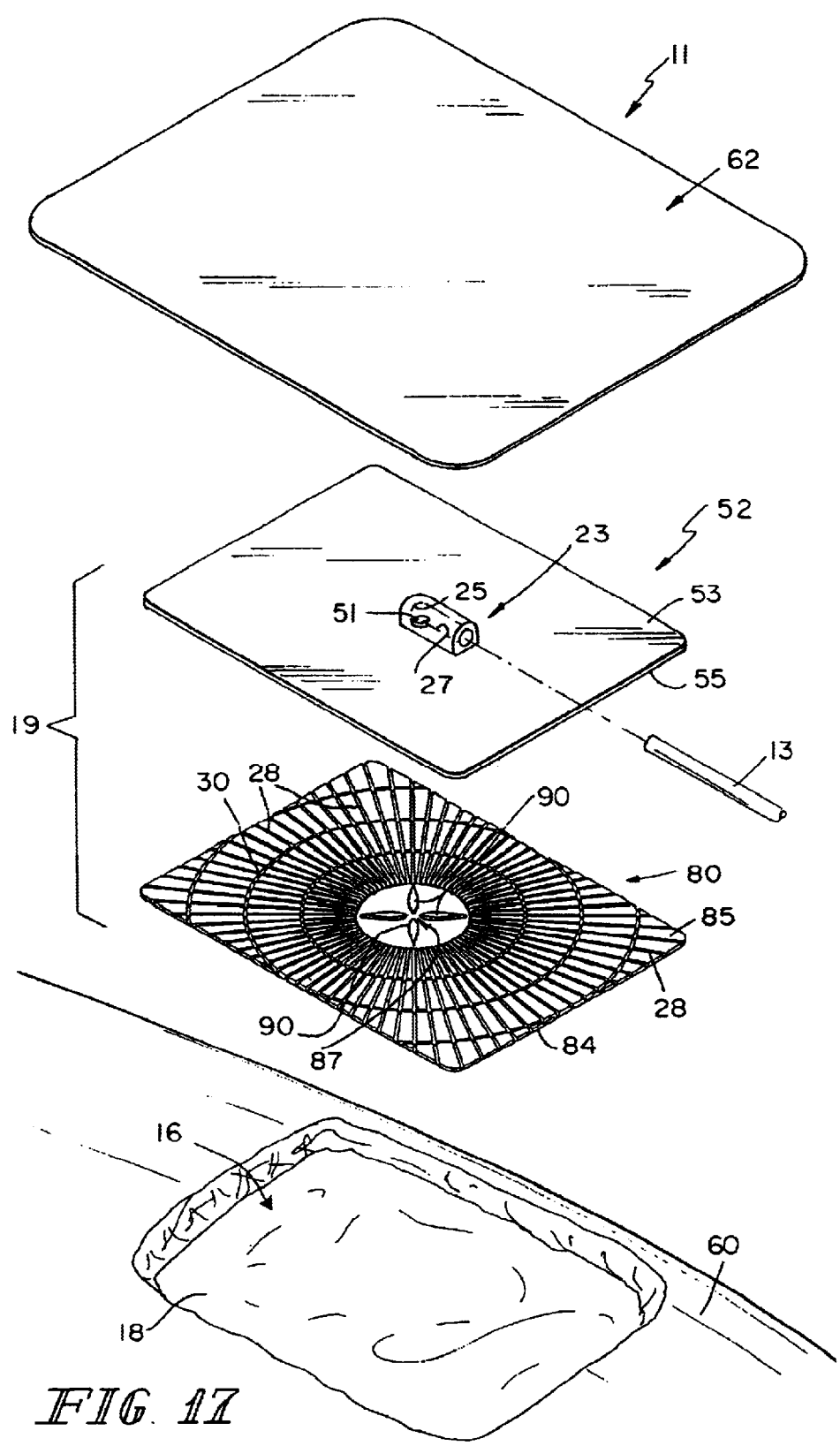
FIG. 17 is an exploded perspective view of another wound care bandage similar to the wound care bandage of FIG. 1 showing the bandage positioned above a wound bed and including a wound contacting layer and a cover of the bandage which cooperate to form a wound dressing member for placement within the wound bed, and also showing sealing film to cover the member and seal about the wound.

Layer 80 includes a wound contacting surface 84 and an upper or opposite surface 85. Wound contacting surface 84, or portions thereof, contacts and generally conforms to the wound surface 18. Opposite surface 85 includes a central area 87 and the same plurality of channels 28, shown previously in FIGS. 2–4 with respect to member 20. Channels 28 extend radially away from central area 87. Central area 87 is similar to central area or port 26 of a member 20 in that central area 87 communicates with port 51 of cover 52. However, central area 87 is recessed relative to the portions of upper surface 84 between channels 28, as shown in FIGS. 18 and 19. As shown in FIGS. 17 and 20, channels 28 are open at the sides and ends of member 19, similar to channels 28 of member 20. Opposite surface 85 further includes concentric channels 30, shown in FIGS. 17, 20 and 21. As shown in FIG. 17, central area 87 of layer 80 is provided to communicate with the vacuum source 12 and irrigation source 14 through cover 52, as will be described below.

A plurality of radially extending protrusions or bosses 90 are positioned around central area 87. Bosses 90 are positioned between central area 87 and channels 28, 30, as shown in FIG. 17. Bosses 90 prevent central area 87 from collapsing in on port 51 of cover 52 and forming an unwanted seal which would effectively block air flow through port 51 while suction is applied to bandage 11. Port 51 communicates with the vacuum source 12 and/or the irrigation source 14 via connecter 23 and tube 13, as shown in FIGS. 17–20. As mentioned above, port 51 is in communication with central area 87 of layer 80.

Illustratively, four bosses 90 are shown in FIG. 17. However, it is within the scope of this disclosure to provide any number of bosses 90 or the like about central area 87 of layer 80 to prevent central area 87 from sealing off port 51 of cover 52 as suction is applied to bandage 11. Further, it is within the scope of this disclosure to include bosses 90 having a tapered cross-section, as shown in FIG. 19, or to include a boss or bosses having any shape that prevents central area 87 from sealing off port 51 when suction is applied to bandage 11. Alternative or supplemental bosses 91 are shown in FIG. 19. Bosses 91 are positioned between bosses 90 and further prevent central area 87 from collapsing on port 51 and forming an unwanted seal blocking air flow through port 51 while suction is applied to bandage 11. Alternative bosses 91 are generally rectangularly shaped and extend inwardly from channels 28 toward central area 87.

Figure 32:
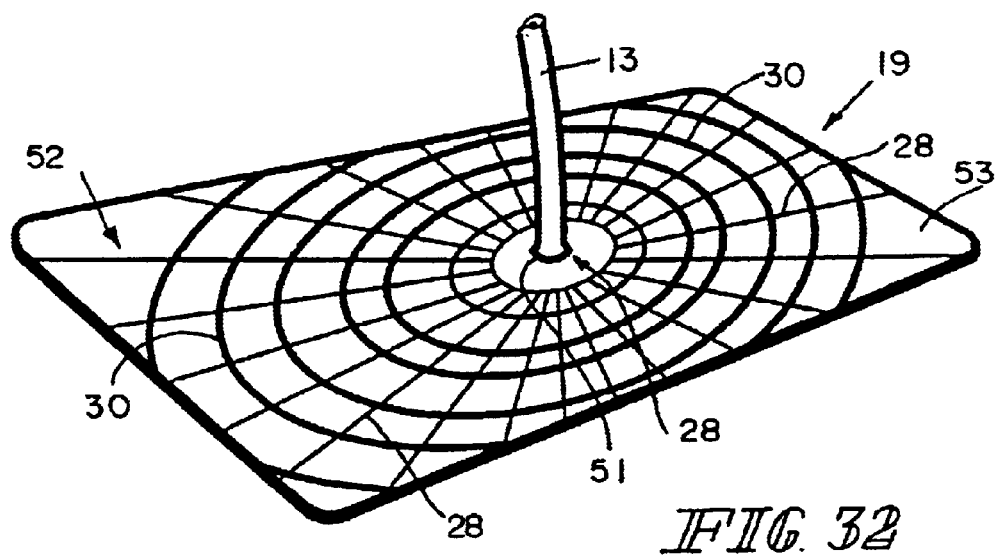
FIG. 32 is a perspective view of another embodiment of the bandage showing a vertical tube attachment at the port of the member.

Connecter 23, as shown in FIGS. 17–19, is a tubal port coupled to a top surface 53 of cover 52 and in communication with port 51 of cover 52. As mentioned before, it is within the scope of this disclosure for connecter 23 to be a separate component of member 19 which is coupled to cover 52 or for connecter 23 to be molded integrally with cover 52. Connecter 23 includes a passageway formed at a right-angle. Thus, the passageway in connecter 23 has a vertical portion 25 that communicates with port 51 and a horizontal portion 27 that communicates with vertical portion 25. Connecter 23 connects with tube 13 to provide a horizontal tube attachment with respect to port 51. A vertical tube attachment is shown in FIG. 32, for example. In FIG. 32, tube 13 is coupled directly to port 51 of cover 52. Cover 52 includes a bottom surface 55 and top surface 53, as shown in FIG. 17. Bottom surface 55 engages opposite surface 85 of layer 80, as shown in FIGS. 18–20.

In some embodiments, member 19 is made by heat sealing opposite surface 85 of layer 80 and bottom surface 55 of cover 52 together and by heat sealing connecter 23 to top surface 53 of cover 52. Member 20 of bandage 10 may also be heat sealed to cover 52. With respect to member 19 of bandage 11, for example, each of connecter 23, cover 52 (or the combination of cover 52 and connecter 23), and layer 80 may be pre-shaped and formed from semi-cured silicone. Once the connecter 23, cover 52, and layer 80 are placed together appropriately, the entire member 19 may be heated to heat seal and cure each of the three components to one another. Alternatively, for example, the cover 52 only may be made from semi-cured silicone while the connecter 23 and layer 80 may be made from fully cured silicone. Once placed together and heated, connecter 23 and layer 80 will heat seal to cover 52. Semi-cured silicon may be bought and pre-molded from a manufacturer such as NuSil Technology, for example. Although the method of heat sealing the cover 52, connecter 23, and layer 80 to each other is disclosed, it is within the scope of this disclosure to form member 19 by coupling layer 80, cover 52, and port 51 together by any other means such as through the use of adhesives, for example. Further, it is within the scope of this disclosure to provide a member 19 where cover 52 lies adjacent to, but is not coupled to, layer 80.

As mentioned above, cover 52 is coupled to layer 80 and connecter 23 is coupled to cover 52 to form member 19. Cover 52 and layer 80 cooperate to form distinct passageways 56 of member 19 defined by channels 28, 30 of layer 80 and bottom surface 55 of cover 52. Passageways 56 are in communication with central area 87 of layer 80 and central area 87 of layer 80 is in communication with port 51 of cover 52 which is in communication with the vacuum and/or irrigation sources 12, 14 via connecter 23 and tube 13. Therefore, passageways 56 are in communication with the vacuum and/or irrigation sources 12, 14.

Figure 21:
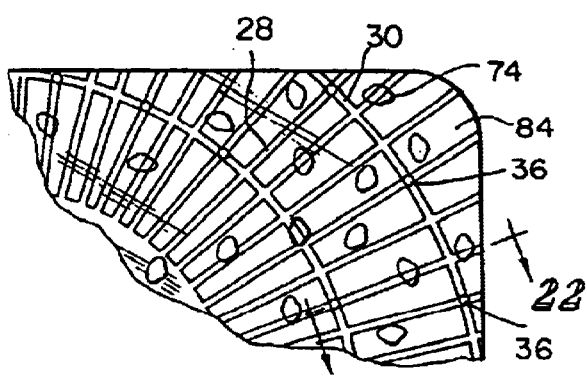
FIG. 21 is a bottom view of a portion of a member having a rough or textured wound contacting surface.
Figure 22:
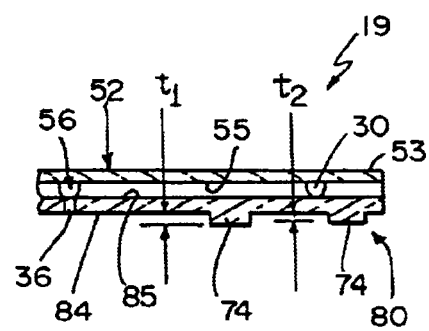
FIG. 22 is a sectional view taken along line 22—22 of FIG. 21 showing the irregular texturing of the wound contacting surface of the member.

Layer 80 (similar to member 20) includes through holes 36 which extend from channels 28, 30 through layer 80 to wound contacting surface 84, as shown in FIGS. 18 and 19. Holes 36 are distinct and are provided to communicate with channels 28, 30 of layer 80. Holes 36 therefore communicate with passageways 56 of member 19 and the vacuum and/or irrigation sources 12, 14 as well to allow the suction from the vacuum source 12 and/or the fluid from the irrigation source 14 to reach the wound surface 18 via the holes 36. As shown in FIGS. 2, 20, and 21, holes 36 have a staggered arrangement. Illustratively, holes 36 are 0.020 inches (0.508 mm) in diameter and are spaced approximately 0.500 inches (12.700 mm) apart along channels 28, 30 of layer 20. It is, however, within the scope of the disclosure to include holes having other suitable sized diameters and/or other suitable spacing that allow for the removal of exudate without clogging. Bandage 11 further includes sealing layer or film 62 that is placed over cover 52 and around tube 13, as shown in FIGS. 1 and 17 and described above with respect to bandage 10. Film 62 may be substantially larger than the wound 16 or member 19 to provide an effective seal about the member 19 and the wound 16. Bandage 11 does not include gauze or packing 58 included in bandage 10.

Illustrative member 19 of bandage 11 includes a smooth wound contacting surface 84, as shown in FIG. 17. Wound contacting surface 84 may also be textured or roughened as illustrated by irregular nubs 74 shown in FIGS. 21 and 22. Nubs 74 may have different dimensions as shown by thickness, t1, and thickness, t2, in FIG. 22. By providing member 19 with a textured or roughened surface, a space is created between surface 84 of layer 80 and wound surface 18. Through holes 36 communicate with this space which permits vacuum source 12 to establish a generally uniformly distributed vacuum or negative pressure to the wound surface 18 to draw blood from the body to the wound surface 18 and to draw exudate from the wound 16 through holes 36, into channels 28, 30 and passageways 56, and out port 51 of cover 52. It is within the scope of this disclosure to include other means for providing a space between surface 84 and wound bed surface 18 such as providing ribs, protrusions, channels, spacers, etc, as described above with respect to member 20 of bandage 10.

The vacuum or negative pressure which draws blood from the body to the wound surface 18 and draws exudate from the wound 16 up through member 19 promotes the healing of wound 16. As wound 16 heals, granulations form along the wound surface 18. Granulations, therefore, are the replacement within the wound bed of tissue lost. As the granulations fill in the wound bed causing the wound 16 to heal, member 19 rides up on the wound surface 18 on top of the granulations which are formed.

Although illustrative bandage 10 includes one central port 40, it is within the scope of this disclosure to include multiple ports. It is further within the scope of this disclosure to provide an illustrative member 619, as shown in FIGS. 35 and 36 and discussed below, having multiple ports and multiple passageway sets for use independent of each other.

Figure 41:
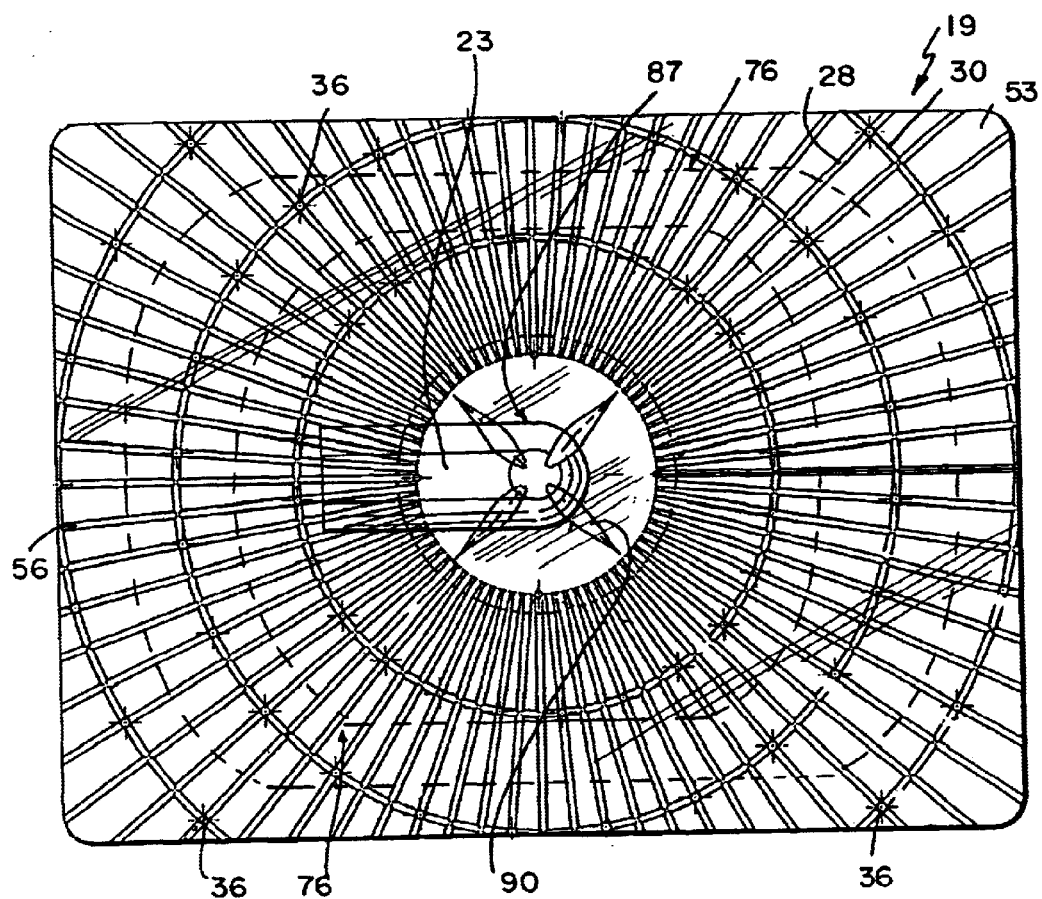
FIG. 41 is a top view of the member of the present invention showing the cover of the member including scale markings to provide a caregiver with a reference point for trimming the member to fit the particular wound of the patient.

In order to accommodate different sized wounds 16, member 19 may be trimmed to fit a particular wound 16. As shown in FIG. 41, some embodiments of member 19 include scale markings 76, indicated by the dotted lines. Scale markings 76 indicate areas where a caregiver may trim member 19 to fit a particular wound 16. Further, the scale markings 76 may denote measurement sizes, for example, to permit a caregiver to cut the member 19 to fit a pre-measured wound 16. Also, as mentioned above, the transparent nature of member 19 is illustrated in FIG. 41.

Figures 23, 24:
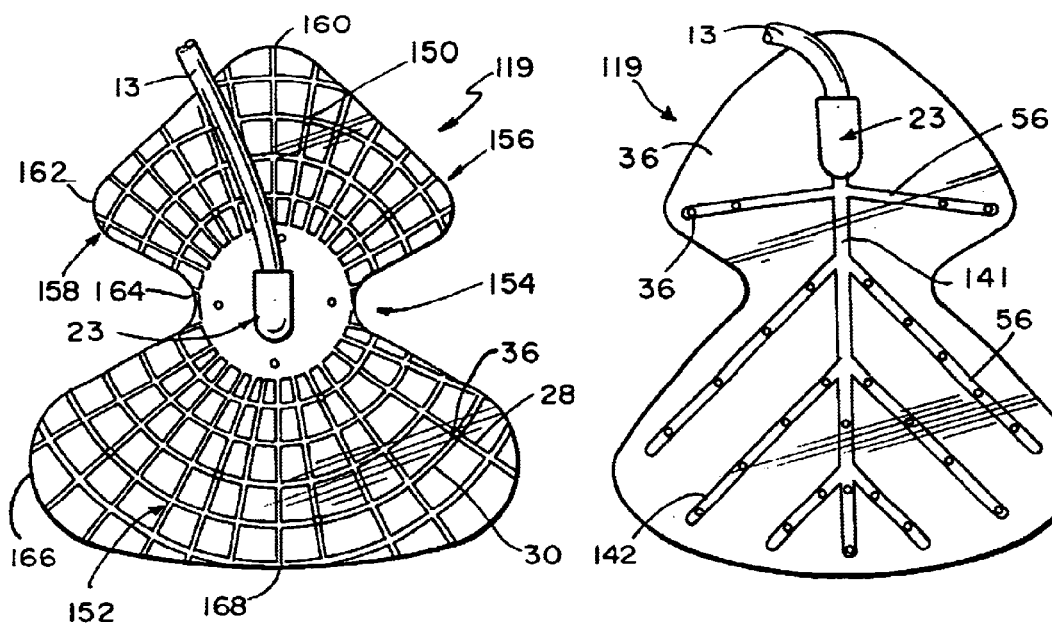
FIG. 23 is a top view of a member showing the member being saddle-shaped for use on a heel, as shown in FIG. 25, for example, and also showing a centrally located connecter coupled to the cover and in communication with a central port of the cover and channels of the wound contacting layer radiating outwardly from the port.
FIG. 24 is a top view of another member, similar to the embodiment of FIG. 23, showing the member being saddle-shaped, a port positioned on an upper portion of the member, and lateral passageways of the member extending outwardly and downwardly from a vertical central passageway of the member.
Figure 25:
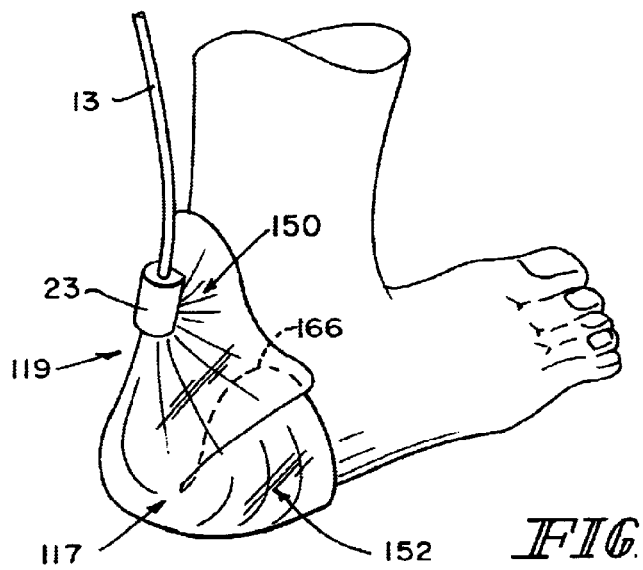
FIG. 25 is a perspective view of the member shown in FIG. 24 positioned around the heel of a patient's foot.

In order to accommodate various types and placements of wounds on patients, member 19 may be provided in various conforming shapes and sizes. For example, illustrative embodiments of a member 119 are shown in FIGS. 23–25 for use with a wound on a patient's heel 117. Member 119 is saddle-shaped and includes a top portion 150, a bottom portion 152, and a neck portion 154 integrally coupled to and spaced between top portion 150 and bottom portion 152, as shown in FIGS. 23 and 24. Member 119 includes a right and a left side 156, 158 which are each shaped to form an inwardly facing "W". Each W-shaped side 156, 158 includes a top point 160, a first trough 162, a peak 164, a second trough 166, and a bottom point 168. The neck portion 154 is positioned between each of the peaks 164.

Member 119 is similar to member 19 and includes a cover (not shown) and a wound contacting layer (not shown) having channels 28, 30 and through holes 36. To form member 119, the cover and layer are each saddle-shaped and include matching W-shaped sides. The cover and layer cooperate to form passageways 56 of member 119 in a manner similar to the manner in which cover 52 and layer 80 (and cover 52 and member 20) cooperate to form passageways 56 in member 19. All similar features between member 19 and alternate member 119 are marked with similar reference numerals. The cover of member 119 includes port 51 formed in top surface 53 of the cover and in communication with connecter 23.

Port 51 and connecter 23 are centrally located and passageways 56 radiate outwardly therefrom in the embodiment of FIG. 23. Illustratively, port 51 and connecter 23 are located on top portion 150 of member 119, the embodiment shown in FIG. 24. Passageways 56 of member 119 shown in FIG. 24 are defined by a central passageway 141 in communication with port 51 of the cover and lateral passageways 142 in communication with central passageway 141. The passageways 56 in the embodiment of FIG. 24 terminate before reaching the peripheral edge of member 119, whereas passageways 56 in the embodiment of FIG. 23 are open at the peripheral edge. As shown in FIG. 25, member 119 is folded to cup the patient's heel 117. In the illustrative cupped configuration of member 119, troughs 162 of top portion 150 overlap troughs 166 of bottom portion 152.

A member 219 is illustratively shown in FIGS. 26 and 27 and is used to treat tunneled wounds such as wound 116. Member 219 includes a truncated cone-shaped portion 250 and a tube-shaped portion 252 coupled to cone-shaped portion 250 at a first end 254. A dome-shaped tip 256 is coupled to tube-shaped portion 252 at a second end 258 of the tube-shaped portion 252.

Member 219 is similar to members 119 and 19 in that member 219 includes a wound contacting layer 220 coupled to a cover 222. Further, wound contacting layer 220 and cover 222 cooperate to form passageways 56 which communicate with port 51 of cover 222 and connecter 23. Wound contacting layer 220 is formed to define through holes 36 which communicate with the passageways 56 of member 219 and with wound bed surface 18 of tunneled wound 116.

Member 219 operates in the same or similar manner as members 119 and 19 in that connecter 23 may be coupled to a vacuum source 12 for establishing a vacuum about the wound bed surface 18 to draw blood up to the wound bed surface 18 and/or to remove exudate from the wound bed surface 18. Connecter 23 may also be coupled to irrigation source 14 to supply fluids such as saline, for example, to the wound bed surface 18. As shown in FIGS. 26 and 27, port 51 and connecter 23 of member 219 are positioned on the cone-shaped portion 250. However, it is within the disclosure to position port 51 and connecter 23 anywhere on member 219.

Another illustrative member 319 is shown in FIGS. 28–30. Member 319 is provided for use with abdominal or sternal wounds 316. FIG. 29 shows member 319 being used to treat a sternal wound 316. As shown in FIGS. 29 and 30, member 319 is generally "V-shaped" and includes a right wing 350 and a left wing 352. Member 319 further includes a central portion 351 having a central passageway 354 and a port 340 coupled to tube 13 for communication with either vacuum source 12 or irrigation source 14. Right and left wings 350, 352 are each coupled to central portion 351. Lateral passageways 356 are formed by the cooperation of a wound contacting layer 320 and a cover 322 of member 319, as shown in FIG. 11. Lateral passageways 356 terminate before reaching the sides or peripheral edges of member 319. However, central passageway 354 is open at both a top and bottom edge of member 19. Through holes 36 are formed in wound contacting layer 320 and are provided for communication between passageways 354 and the wound surface 18. Although the communication between the wound surface 18 and the vacuum source 12 and/or irrigation source 14 is provided through central and lateral passageways 354, 356, as shown in FIG. 28, it is within the scope of this disclosure to provide a member 319 for use with abdominal and/or sternal wounds having a different passageway structure for communicating the vacuum source 12 with the wound surface 18. Further, although member 319 is V-shaped, it is within the scope of this disclosure to include a generally flat member which is flexible to adjust to the contour of the sternal or abdominal wound to which it is applied.

Figure 31:
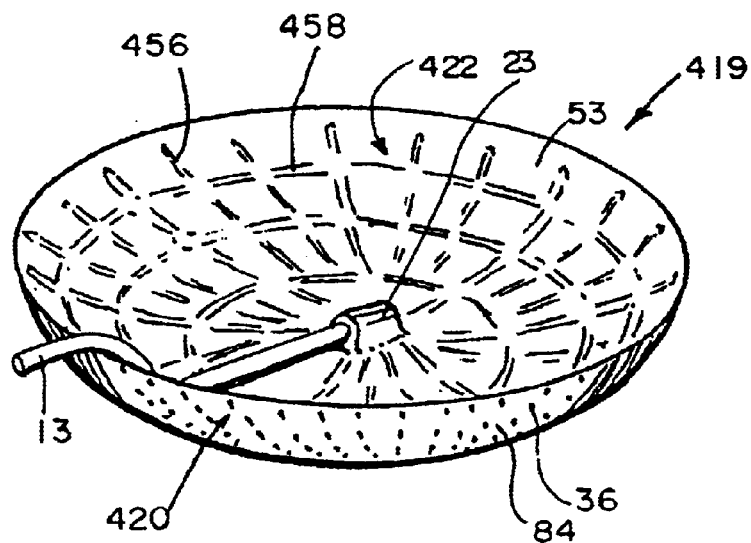
FIG. 31 is a perspective view of yet another embodiment of the member of the present invention showing the member being dome-shaped and having a convex wound contacting surface.

Yet another illustrative embodiment is shown in FIG. 31 where a generally dome-shaped member 419 is provided for use with deep wounds having a wound surface including side walls, for example. Dome-shaped member 419 is able to conform to side portions of a deeper wound bed, for example, to provide the side portions of the wound surface, as well as the bottom portion of the wound surface with suction and irrigation treatment. A port (not shown, but similar to port 51) is centrally located within member 419 and passageways 456 in communication with connecter 23 extend radially therefrom, as shown in FIG. 31. Concentric passageways 458 positioned around the port are also provided. Member 419 includes a cover 422 and a wound contacting layer 420 including a convex wound contacting surface 84 and through holes 36 in communication with passageways 456, 458. Wound contacting surface 84 is premolded to form the convex shape.

Figure 33:
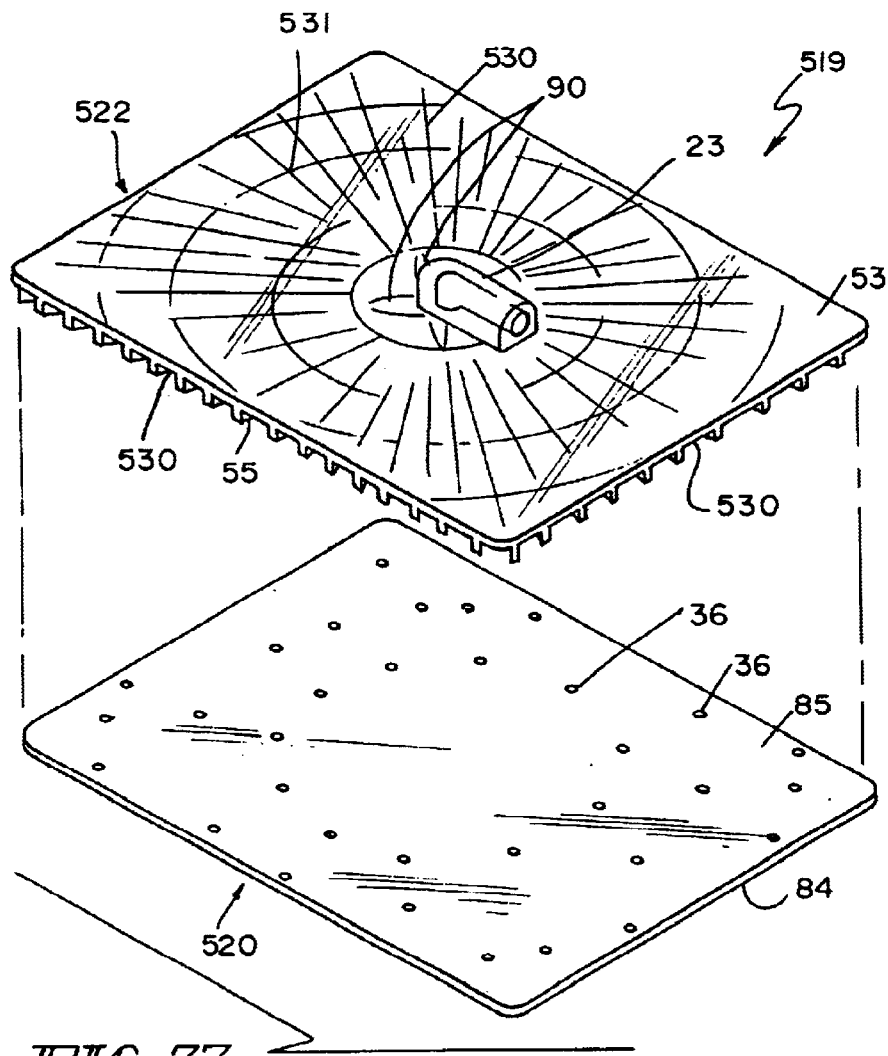
FIG. 33 is an exploded perspective view of another embodiment of the member showing a cover of the member having channels formed therein and also showing a wound contacting layer of the member having a smooth surface and thru holes for communication with the channels of the cover.
Figure 34:
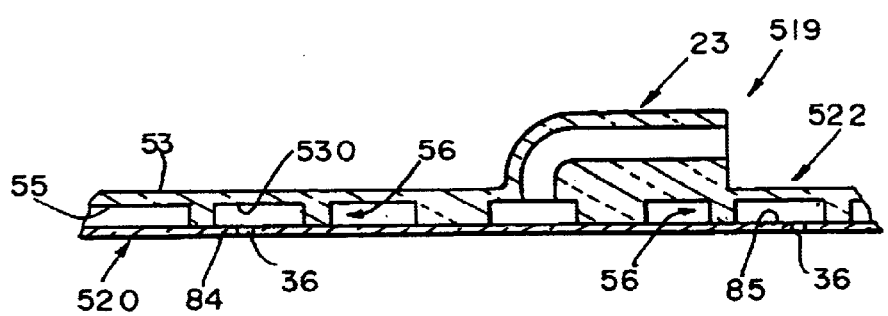
FIG. 34 is a sectional view of a portion of the member of FIG. 33.

As mentioned above and shown in FIGS. 17–22, member 19 includes a wound contacting layer 80 and a cover 52 coupled to the wound contacting layer 80 to form passageways 56. Passageways 56 are formed by the cooperation of layer 80 and cover 52. Specifically, passageways 56 are defined by the channels 28, 30 of layer 80 and the bottom surface 55 of cover 52 which covers and closes each channel 28, 30 to form passageways 56. It is within the scope of this disclosure, however, to form passageways 56 between a wound contacting layer 520 and a cover 522, as shown in FIG. 33, for example. A member 519, as shown in FIGS. 33 and 34, includes wound contacting layer 520 and cover 522 coupled to wound contacting layer 520. Connecter 23 is coupled to top surface 53 of cover 522 and is in communication with port 51 of cover 522. Cover 522 further includes a plurality of channels 530 radiating from port 51 and a plurality of concentric channels 531 formed around port 51. Further, cover 522 includes bosses 90 coupled to bottom surface 55.

Wound contacting layer 520 includes through holes 36. Opposite surface 85 of layer 520 is smooth such that passageways 56 are formed when layer 520 and cover 522 are coupled together. Effectively, member 19 and member 519 each include a port 51 in communication with vacuum source 12 and/or irrigation source 14, passageways 56 in communication with port 51 and connecter 23, and holes 36 in communication with passageways 56 and formed through wound contacting layers 80, 520. Member 19 and member 519 each further include bosses 90 to prevent port 51 from becoming sealed off by central area 87 when suction is applied to bandage 11. Bosses 90 provide an uncollapsable space in central area 87 between port 51 and passageways 56.

Members 19, 119, 219, 319, 419, and 519 discussed above are illustratively each provided for use with vacuum source 12 and irrigation source 14. As illustrated, these embodiments are provided with one port 51 for communication with either the vacuum source 12 or the irrigation source 14 or both. However, a member 619 is shown in FIGS. 35 and 36 and includes port 51, cover 52, layer 80 having a smooth or textured wound contacting surface 84, and an irrigation layer 650 coupled to surface 84 of layer 80. Irrigation layer 650 includes an irrigation port 652 for communication with irrigation source 14, as shown diagrammatically in FIG. 36. Irrigation layer 650 includes an upper surface 654 and a lower surface 656. As shown in FIG. 36, lower surface 656 is positioned to lie adjacent to the wound bed surface 18 and upper surface 654 is coupled to surface 84 of layer 80. As illustrated in this embodiment, layer 80 does not contact the wound bed surface 18; layer 80 acts as an intermediate layer positioned between cover 52 and irrigation layer 650. Irrigation layer 650 lies on the wound bed surface 18.

Further, irrigation layer 650 includes a plurality of channels 656 formed in upper surface 654 in communication with irrigation port 652 via a central channel 658 which is also formed in upper surface 654. Irrigation through holes 660 are formed in irrigation layer 650 and are positioned to lie within channels 656 and central channel 658. Fluid from irrigation source 14 flows through irrigation port 652 to central channel 658 and lateral channels 656, and finally flows through irrigation holes 660 to the wound bed surface 18, as shown in FIG. 36. Irrigation layer 650 further includes vacuum holes 662 positioned around channels 656, 658. Vacuum holes 662 communicate with the wound bed surface 18 and with through holes 36 of intermediate layer 80. Vacuum holes 662 do not directly communicate with channels 656, 658 of irrigation layer 650. Irrigation layer 650 is illustratively made from the same material as cover 52 and intermediate layer 80 such as silicone, for example.

Cover 52 and layer 80 are the same cover and layer 22, 80 as those shown in FIG. 17 and discussed above. Connecter 23 coupled to cover 52 is provided for communication with vacuum source 12. When cover 52, intermediate layer 80, and irrigation layer 650 are coupled together, as shown in FIG. 36, passageways 56 are formed between cover 52 and intermediate layer 80, as discussed above, and irrigation passageways 664 are formed between surface 84 of layer 80 and upper surface 654 of intermediate layer 650. Passageways 56 are in communication with vacuum source 12 while passageways 664 are in communication with irrigation source 14. As shown in FIG. 36, fluid flows into passageways 664 and out irrigation holes 660 to reach wound bed surface 18. This irrigation fluid and exudate from the wound surface 18 is then sucked up through vacuum holes 662 of irrigation layer 650 and through holes 36 of layer 80 to passageways 56 and finally out port 51 of cover 52. Member 619 allows simultaneous delivery of irrigation fluid to the wound surface 18 and application of suction to the wound bed surface 18 through separate and distinct passageways. Although the particular structure of member 619 is shown in FIGS. 35 and 36 and discussed above, it is within the scope of this disclosure to include any member having separate and distinct passageways for delivering fluid to and drawing a vacuum on the wound surface 18. It will be appreciated that, in some circumstances, the irrigation and suction may take place simultaneously.

Yet another illustrative member 719 is shown in FIGS. 37 and 38 including a wound contacting layer 80 and a cover 52 coupled to the layer 80. Member 719 further includes a filament or wire form 78 molded into the body of cover 52, as shown in FIG. 38, for example. Wire form 78 is provided to allow for a caregiver to mold member 719 into a desired shape, such as to the shape of the wound 16, for example. Member 719 will retain that shape due to the wire form 78 molded into the cover 52. Illustrative wire form 78 is a metal grid, as shown in FIG. 37; however, it is within the scope of this disclosure to include any type or configuration of a filament, fine screen, or wire form which retains its shape once formed to fit a particular shape as desired by the caregiver. Further, it is within the scope of this disclosure for the wire form 78 to be molded into either wound contacting layer 80 (or member 20) or cover 52 or both. Further it is within the scope of this disclosure to include wire form 78 molded into the cover and/or wound irrigation layer of any of the previously disclosed embodiments.

Yet another illustrative member 819 is shown in FIGS. 39 and 40. A wound contacting layer 820 includes an adhesive 850 about the outer perimeter of wound contacting surface 84 of layer 820. As shown in FIG. 40, cover 52 is coupled to opposite surface 85 of layer 820 and connecter 23 is coupled to top surface 53 of cover 52. Adhesive 850 is provided to seal to the patient's healthy skin 60 surrounding wound 16. Adhesive 850, therefore, permits member 819 to be selfsealing such that a vacuum or negative pressure can be created above wound surface 18 without the use of sealing film 62. In order for adhesive 850 to be able to effectively seal to healthy skin 60, passageways 56 of member 819 are not formed to extend to the peripheral edges of member 819 unlike passageways 56 of member 19 which do extend to the peripheral edges of member 19. Although adhesive 850 is shown to be coupled to layer 820, it is within the scope of this disclosure to provide any member having an adhesive for attachment to the patient's healthy skin surrounding the wound so that the member is self-sealing and able to maintain a negative pressure above the wound without the use of a sealing film. For example, the wound contacting layer may be sized smaller than the cover and the bottom surface of the cover may include an outer adhesive perimeter for coupling with the patient's surrounding healthy skin.

Although this invention has been described in detail with reference to certain embodiments, variations and modifications exist within the scope and spirit of the invention as described and defined in the following claims.

What is claimed is:

1. A thin, flexible member for use in a vacuum bandage connected to a vacuum source and for use with a wound having a wound surface, the member comprising:

a wound contacting surface adapted to be in contact with and generally conform to the wound surface, a plurality of discrete holes formed in the wound contacting surface, a port configured to communicate with the vacuum source, and communicating means from the holes to the port, the member being formed from a generally non-porous material.

2. The member of claim 1, wherein the communicating means comprises a distinct passageway between each hole and the port.

3. The member of claim 2, wherein the member includes a wound contacting layer having channels formed therein and a cover coupled to the wound contacting layer, and wherein the cover cooperates with the channels in the wound contacting layer to define the distinct passageways.

4. The member of claim 3, further including a boss positioned near the port of the cover to prevent an upper surface of the wound contacting layer from sealing off the port when the vacuum source is applied.

5. The member of claim 4, wherein the wound contacting layer includes multiple bosses spaced around the port of the cover and wherein each boss has a tapered cross-section.

6. The member of claim 3, wherein the cover and the wound contacting layer are each made from a transparent and non-porous material.

7. The member of claim 3, further including an outer perimeter configured adhesively to seal about the wound to a patient's healthy skin surrounding the wound.

8. The member of claim 3, wherein the cover is formed to include the port, and the member further including a connecter coupled to the cover for communication with the port and configured for communication with the vacuum source, the connecter defines a right angled passageway to provide a tube attachment extending along a patient's healthy skin surrounding the wound.

9. The member of claim 2, wherein the wound contacting surface is textured to provide a vacuum space between the wound contacting layer and the wound surface.

10. The member of claim 8, wherein the cover includes scale markings for a caregiver to trim the member to fit a particular wound.

11. The member of claim 2, further including a plurality of irrigation passageways configured for communication with an irrigation source and with the wound surface and distinct from the passageways configured for communication with the vacuum source, and an irrigation port in communication with the irrigation passageways and adapted for communication with the irrigation source.

12. The member of claim 1, wherein the member further includes a wound contacting layer and a cover coupled to the wound contacting layer.

13. The member of claim 12, wherein the wound contacting layer includes a plurality of channels in communication with the port and the holes and which cooperate with the cover to form passageways which define the communicating means.

14. The member of claim 13, wherein the port is centrally located and the channels extend radially outwardly from the port.

15. The member of claim 13, wherein the wound contacting layer and the cover are each made from a generally non-porous material.

16. The member of claim 12, further including a wire form coupled to one of the wound contacting layer and the cover.

17. The member of claim 16, wherein the wire form is molded into the cover.

18. The member of claim 16, wherein the wire form is molded into the wound contacting layer.

19. The member of claim 12, wherein the communicating means is defined by a plurality of channels formed in the cover which cooperate with the wound contacting layer to form a passageway between the port and each of the holes.

20. The member of claim 1, wherein the member is saddle-shaped and adapted for use with a wound on a patient's heel.

21. The member of claim 20, further including an upper portion, a neck portion coupled to the upper portion, and a lower portion coupled to the neck portion.

22. The member of claim 21, wherein the port is located in the neck portion and the communicating means comprises a plurality of passageways extending radially from the port.

23. The member of claim 21, wherein the port is located in the upper portion and the communicating means comprises a central passageway extending from the port and plurality of lateral passageways extending from the central passageway.

24. The member of claim 20, further including two inwardly facing "W-shaped" sides.

25. The member of claim 1, wherein the member includes a cone-shaped portion, a tube-shaped portion coupled to the cone-shaped portion, and a dome-shaped portion coupled to the tube-shaped portion, and wherein the member is adapted for use with a tunneled wound.

26. The member of claim 25, wherein the port is positioned in the cone-shaped portion.

27. The member of claim 1, wherein a cross-section of the member is generally "V-shaped" and the member includes a right-wing, a left-wing, and a central portion coupled to the right-wing and the left-wing.

28. The member of claim 27, wherein the communicating means comprises a plurality of passageways defined by a central passageway along the central portion in communication with the port and lateral passageways in communication with the central passageway and the holes, the central passageway being disposed between the right-wing and the left-wing.

29. The member of claim 1, wherein the wound contacting surface is generally dome-shaped.

30. A non-porous wound dressing member for use in a vacuum bandage on a wound surface and coupled to a vacuum source, the member comprising
 a wound contacting layer having a wound contacting surface adapted to be in contact with and generally conform to the wound surface, an opposite surface, a plurality of channels formed in the opposite surface, and at least one hole between the wound contacting surface and each channel, and
 a cover coupled to portions of the opposite surface of the wound contacting layer between the channels and formed to define a port in communication with the channels, the port being configured to communicate with the vacuum source, the cover and the channels in the opposite surface of the layer cooperating to form a passageway from the port to each of the holes.

31. The member of claim 30,wherein the member is fabricated from a non-porous and non-absorptive material.

32. The member of claim 31, wherein the material is non-adhesive with respect to the wound surface.

33. The member of claim 31, wherein the material is generally non-compressible.

34. A thin, flexible member for use in a vacuum bandage connected to a vacuum source and for use with a wound bed having a wound surface, the member comprising:
 a first set of passageways adapted for communication with the vacuum source and the wound surface, and
 a second set of passageways distinct from the first set adapted for communication with an irrigation source and the wound surface,
 the thin, flexible member being adapted to be in contact with and generally conform to the wound surface.

35. The member of claim 34, wherein the member includes a cover, an irrigation layer, and an intermediate layer positioned between the cover and the irrigation layer.

36. The member of claim 35, wherein cover includes a port configured for communication with the vacuum source, the intermediate layer includes vacuum channels in communication with the port and vacuum holes in communication with the channels, and the irrigation layer includes an irrigation port adapted for communication with the irrigation source, irrigation channels in communication with the irrigation port, irrigation holes in communication with the irrigation channels and adapted for communication with the wound surface, and vacuum holes in communication with the vacuum holes of the intermediate layer and adapted for communication with the wound surface.

37. A thin, flexible wound dressing member for use in a vacuum bandage connected to a vacuum source and for use with a wound having a wound surface, the member comprising:

a wound contacting surface adapted to be in contact with and generally conform to the wound surface, a plurality of discrete holes formed in the wound contacting surface, a port configured to communicate with the vacuum source, and a passageway from the port to each hole, and the member being configured to remain on top of granulations formed by the wound throughout vacuum therapy treatment of the wound without connecting to the granulations.

* * * * *